US010066089B2

(12) United States Patent
Belalcazar Otalora

(10) Patent No.: US 10,066,089 B2
(45) Date of Patent: Sep. 4, 2018

(54) COFFEE PULP PRESERVATION AND EXTRACTION PROCESS

(71) Applicant: Pectcof B.V., Wageningen (NL)

(72) Inventor: Andres Felipe Belalcazar Otalora, Amsterdam (NL)

(73) Assignee: Pectof B.V., Wageningen (NL)

( * ) Notice: Subject to any disclaimer, the term of this patent is extended or adjusted under 35 U.S.C. 154(b) by 209 days.

(21) Appl. No.: 15/039,618

(22) PCT Filed: May 27, 2014

(86) PCT No.: PCT/EP2014/060919
§ 371 (c)(1),
(2) Date: May 26, 2016

(87) PCT Pub. No.: WO2015/078594
PCT Pub. Date: Jun. 4, 2015

(65) Prior Publication Data
US 2017/0145193 A1 May 25, 2017

(30) Foreign Application Priority Data

Nov. 27, 2013 (WO) .................. PCT/EP2013/074811

(51) Int. Cl.
*A23F 5/02* (2006.01)
*C08L 5/06* (2006.01)
(Continued)

(52) U.S. Cl.
CPC .............. *C08L 5/06* (2013.01); *A23F 5/163* (2013.01); *A23F 5/166* (2013.01);
(Continued)

(58) Field of Classification Search
CPC ........................................................ A23F 5/02
See application file for complete search history.

(56) References Cited

U.S. PATENT DOCUMENTS

| 4,672,034 A | 6/1987 | Rombouts et al. |
| 2003/0220485 A1 | 11/2003 | Ni et al. |

FOREIGN PATENT DOCUMENTS

| WO | WO 96/03440 | 2/1996 |
| WO | WO 00/27888 | 5/2000 |
| WO | WO 2011/073522 | 6/2011 |

OTHER PUBLICATIONS

Buchholt et al., "Preparation and properties of enzymatically and chemically modified sugar beet pectins," Carbohydrate Polymers, Applied Science Publishers, Ltd. Barking, GB, vol. 58, No. 2, pp. 149-161 (2004).

(Continued)

*Primary Examiner* — Rosanne Kosson
(74) *Attorney, Agent, or Firm* — Occhiuti & Rohlicek LLP

(57) ABSTRACT

The invention provides a coffee pulp treatment process comprising (a1) Providing coffee pulp, obtainable from a production process for producing green coffee beans from coffee cherries; (a2) subjecting the coffee pulp to a preservation process, (b) extracting from the coffee pulp a pectin comprising extract, wherein extraction is performed under acid conditions or alkaline conditions, to provide the pectin comprising extract; (c) enzymatic treatment of the pectin comprising extract, wherein the enzymatic treatment comprises a treatment with one or more enzymes selected from the group consisting of an esterase and a reductase, to provide a enzymatically treated pectin material; and (d) extraction of polyphenol functionalized coffee pectin extract from the enzymatically treated pectin material.

13 Claims, 11 Drawing Sheets

(51) Int. Cl.
  *C08B 37/00* (2006.01)
  *C12P 19/04* (2006.01)
  *A23F 5/16* (2006.01)
  *C12P 19/44* (2006.01)
(52) U.S. Cl.
  CPC ...... *C08B 37/0045* (2013.01); *C08B 37/0048* (2013.01); *C12P 19/04* (2013.01); *C12P 19/44* (2013.01); *C12Y 111/01* (2013.01); *C12Y 301/00* (2013.01)

(56) References Cited

OTHER PUBLICATIONS

Calle, "Métodos de extracción de las pectinas del café" Cenicafé (Columbia) vol. 13, No. 2 pp. 69-74 (1962).
Esquivel et al., "Functional properties of coffee and coffee by-products," Elsevier, Food Research International 46 (2012) 488-495.
Fissore et al., "Rheological performance of pectin-enriched products isolated from *red beet* (L. var.) through alkaline and enzymatic treatments," Fiid Hydrocolloids, vol. 26, No. 1, pp. 249-260 (2012).
Hendriks et al, "Pretreatments to enhance the digestibility of lignocellulosic biomass," Elsevier, Bioresource Technology 100 (2009) 10-18.
Instituto Centroamericano De Investigacion Y Tecnologia Industrial (icaiti): "Industrialization of coffee pectin," Jun. 1986 [retrieved from the internet Jun. 25, 2014]: http://pdf.usaid.gov/pdf_docs/PDAAW317.pdf.
McManus et al., "Polyphenol interactions. Part 1. Introduction; Some observations on the reversible compexation of polyphenols with proteins and polysaccharides," J. Chem. Soc., Perkin Trans. II (1985).
Murillo et al., "Effect of bisulfate addition on the chemical composition and cellular content fractions of dehydrated coffee pulp," Journal of Agriculture and Food Chemistry, vol. 25, No. 5, pp. 1090-1092 (1977).
Oosterveld et al., "Formation of ferulic acid PC dehydrodimers through oxidative cross-linking of sugar beet pectin," Elsevier Science Ltd, Carbohydrate Research 300 (1997) 179-181.
Rombouts et al., "Feruloylated Pectic Substances from Sugar-Beet Pulp," Carbohydrate Research, 154 (1986) 177-187.
Schmelter et al., "Enzymatic modifications of pectins and the impact on their rheological properties," Carbohydrate Polymers, Applied Science Publishers, Ltd., Braking GB, vol. 47, No. 2, pp. 99-108, (2002).
Strafford et al., "Inhibition of spoilage mould conidia by acetic acid and sorbic acid involves different modes of action, requiring modification of the classical weak-acid theory," International Journal of Food Microbiology, vol. 136, No. 1, pp. 37-43 (2009).
Wehr et al., "Alkali hydroxide-induces gelatin of pectin," Food Hydrocolloids, vol. 18, No. 3, pp. 375-378 (2004).

COFFEE PULP PRESERVATION AND EXTRACTION PROCESS

CROSS REFERENCE TO RELATED APPLICATIOIN

This application is the national phase under 35 USC 371 of international application no. PCT/EP2014/060919, filed May 27, 2014, which claims the benefit under 35 USC § 120 international application no. PCT/EP2013/074811, filed Nov. 27, 2013. The contents of the aforementioned applications are incorporated herein in their entirety.

FIELD OF THE INVENTION

The invention relates to a coffee pulp treatment process as well as to the product(s) obtained with such process.

BACKGROUND OF THE INVENTION

With the production of coffee, coffee pulp is produced. Regardless of the source (wet or dry processing), by-products and waste products are often problematic. For example, pulp and mucilage are relatively acidic, corrosive to equipment, and difficult to safely dispose. Furthermore, where the pulp is discarded in a landfill or other disposal site, rotting pulp may lead to unpleasant smells. Therefore, by-products and waste products have often been viewed as materials which are either unusable, hazardous, or of negligible value.

WO2004098320 describes a method for isolating a nutrient from coffee cherries or for producing a food product that comprises a coffee cherry or portion thereof. In WO2004098320, it is particularly preferred that coffee cherries will have an extremely low concentration of mycotoxins, including various aflatoxins, fumonisins, ochratoxins, and/or vomitoxin (DON, deoxynivalenol).

SUMMARY OF THE INVENTION

As will be clear from the above, and as also further indicated below, there is a desire to make the coffee production process greener, especially by an economic reuse of parts of the by-products of the process, such as coffee pulp. In the process to obtain green coffee beans, a major stream of biomass is produced. This biomass is rich in useful bio compounds; however, a technology really commercially ready for the recovery and use of these compounds is not available. Moreover, the high amounts of toxic compounds (mostly polyphenols and caffeine) in the streams make the biomass an environmental problem in the coffee producing regions. First some general comments are given below.

After collection of the coffee cherries, the coffee cherries are subjected to various processes to obtain the green coffee bean (i.e. non-roasted coffee bean). Most of the world coffee production is processed in two ways; the dry method and the wet method.

In the wet method, the cherries are collected and pulped fresh, leaving the mucilage (endocarp) and the silver skin attach to the beans; after pulping the beans go to fermentation tanks for period in general in the range of 12-24 h in which the mucilage is released from the beans and silver skin. The beans then are dried (sun or hot air dried), the silver skin is removed and the green beans are packed and stored for further trade. During these processes about 45% of the coffee cherry biomass is discarded as waste material. This biomass has high content of polyphenols and caffeine, and therefore becomes toxic in high concentrations. Although composting is an alternative, big extensions of land and hard labor are necessary. On top of these requirements, the high concentration of polyphenols makes of the use of this compost a poor fertilizer with the risk of poisoning the soil and making it acidic.

Hence, the term "coffee pulp" herein especially refers to the pulp obtained after cherry processing. Therefore, the term "coffee pulp" might also refer to "coffee cherry pulp". Further, the term "coffee pulp" may also include discarded unripe and overripe cherries, not usable in the production of (high) quality green beans. Hence, the term coffee pulp may especially refer to one or more of pulp obtained after cherry processing, discarded unripe cherries not usable in the production of (high) quality green beans and discarded overripe cherries not usable in the production of (high) quality green beans. The coffee pulp may relate to one or more of the exocarp, outer mesocarp (the pulp itself), and the mesocarp (mucilage or parchment). The hull (also known as silver skin or parchment) is not taken into account. Note that the silver skin is part of the seed, not part of the pericarp. The pericarp is especially composed of the skin (exocarp), pulp (outer mesocarp), mucilage (endocarp). The silver skin is part of the endosperm. It is further referred to amongst others Esquivel et al, "Functional properties of coffee and coffee by-products", Food Research International 46 (2012) 488-495, which is incorporated herein by reference. Especially, the coffee pulp is a by-product from the wet method processing, or a semi-dry processing, of coffee beans.

In the dry method, the coffee cherries are dried, especially under the sun, for—in general—several days. Thereafter, the dried pulp is separated from the green beans by pulping. This method does not easily allow control of the drying process and may therefore generate a low(er) quality coffee.

Most of the coffee nowadays is processed using the wet method (see above) with variations to lower water consumption and control over the drying process (semi-dry, natural pulping etc.). Nevertheless, relative large amounts of biomass are still dumped into rivers.

Nowadays, most of the coffee pulp goes without treatment directly to huge waste disposal sites without any treatment, eventually toxic compounds from the fermenting cherries leach to the rivers, polluting the sources of water in the coffee producing regions. Coffee pulp therefore poses a serious environmental problem, and is a challenge to the sustainability of the coffee supply chain. With the actual production of coffee reaching 10 million tons per year, technology to exploit this waste stream is necessary. Currently coffee pulp is in general used only as compost. There has been research in the use of coffee pulp as feed for dairy cattle in Central and South Americas. Nevertheless, these practices use only a small percentage of the whole stream due to the anti-nutritional and toxic compounds in the biomass. Further, it has been suggested in the art to use crude fibers from coffee pulp as well as other sub products from this biomass. However, there is no known technology in the extraction separation and modification of pectin from coffee pulp and mucilage.

Coffee pulp represents 45% of the total weight of the coffee cherry. The pulp biomass is rich in carbohydrates, polyphenols and caffeine. Because the high contents of organic acids, cathechins, and tannins, the coffee pulp and process water pose a serious environmental problem in the regions where production takes place. Coffee discarded streams (the pulp and process water used to separate the mucilage from the bean in the wet milling factories) have a high BOD (biochemical oxygen demand), which threatens water sources. One of the components of coffee pulp is pectin. Pectin is amongst others known in the food industry as gelling agent. However, pectin from coffee pulp has been reported as a poor gelling agent and therefore not useful in food and pharmaceutical applications. It is theorized that the poor gelling properties are a result of the short length of the pectin backbone, the low molecular weight of the pectin and the high degree of acetylation of the native pectin in the pulp and mucilage of coffee cherry.

After the production of the coffee pulp and before the processing of the coffee pulp in valuable material, it may be desirable to store the coffee pulp and the coffee pulp after production may not always be processed immediately, such as in the case of different sites for production and processing. It appears that coffee pulp relatively quickly deteriorates, which may lead to a lower result in the subsequent process and/or inferior products from the subsequent process. Hence, there is a need for a preservation process of coffee pulp. Further, there is a need for an integral preservation and upgrading process of the coffee pulp.

Hence, it is an aspect of the invention to provide an alternative coffee pulp treatment process, which preferably further at least partly obviate one or more of above-described drawbacks. It is further an aspect of the invention to provide an alternative pectin, derived from coffee pulp, that can be used in food applications as gelling agent and/or that may have other useful applications (like emulsifier). It is further an aspect of the invention to provide a solution to the coffee pulp, by which the coffee production process can become environmentally more sustainable. Hence, the present invention especially includes a coffee pulp treatment process that allows (longer) storage of the coffee pulp.

The present invention may also include the extraction and use of at least one compound extracted from the pulp and mucilage after depulping and washing of the bean, in the wet or semi dry process of green coffee production. Advantageously, the extraction of this bio compound will reduce concentration of toxic compounds in the processing water of coffee de-pulping facilities. Further, the extracted compounds in which pectin is the main component, is a high value ingredient for the food and/or pharmaceutical industries. Further, it surprisingly appears that the extracted bio compounds show the possibility to be tailored for specific purposes due to the diversity of polysaccharides contained in the extracted pectin fraction. The pectin obtained with the process of the invention may allow applications like as prebiotic as well as gelling agents, but also as mesh for surgical implants are among the possible uses of the compounds extracted according to the invention. Further, the pectin obtained may be used as thickener or emulsifier.

The technology suggested here aims for the extraction of pectin from coffee pulp, and optionally modification (i.e. functionalization) of the (extracted) pectin with enzymes. Such modification may include demethylation and/or cross-linking the pectins through the esterified groups. The technology presented here especially aims for the extraction of pectin from coffee pulp, and optional modification of the same pectin with enzymes, to crosslink the pectins through the esterified groups. The enzymatic modifications surprisingly appear to improve the hydro colloidal properties of the extracted pectin. The properties of the resulting pectin are very attractive. In the process, the remaining waste stream may amongst others be detoxified through the hydrolization of tannins, polymerization of phenols and removal of caffeine during the process; this will leave the streams with a substantially reduced BOD (biological oxygen demand) and COD (chemical oxygen demand). Therefore, the environmental impact of coffee production will diminish. The approach may also generate income from the exploitation of the biomass waste as a by-product of the coffee chain. The current invention may significantly contribute to improve the sustainability of a major global commodity. Hence, the invention provides a biorefinery approach in which green chemistry and biotechnology is applied. The process steps may consist of preservation of coffee pulp at the country of production, shipment to a processing site, separation and purification of the products, and commercialization of these products in their perspective markets. A market may be the market of food ingredients, wherein high quality pectin as a potential replacement of Arabic Gum is suggested. With the present innovative technology the coffee pectin can be tailored to meet the standards of different types of applications in the food and pharmaceutical industry. The caffeine content in the remaining waste may advantageously be below 10 ppm, such as even below 1 ppm. Hence, the removal of caffeine may be very efficient while on the other hand also a useful pectin product is provided.

It is known that polyphenols in high concentration can be toxic to cattle, inhibit fermentation and growth of microorganism. Advantageously, in the disclosed invention the presence of polyphenols is actually desired to allow the modification of the pectin without destroying the biopolymer. The technology is the best alternative at the moment, for the management and exploitation of coffee waste. Therefore, the disclosed technology might be adopted at a big scale.

Hence, in a first aspect the invention provides a coffee pulp treatment process comprising: (a1) providing coffee pulp ("pulp"), obtainable from a production process for producing green coffee beans from coffee cherries; (a2) subjecting the coffee pulp to a preservation process comprising one or more of (1) combining the coffee pulp with a preservation liquid comprising a sulfite and a divalent cation and bringing the pH of the thus obtained mixture at 4 or lower, and subsequently removing liquid from the mixture, and (2) heating the (thus obtained) coffee pulp to a temperature of at least 60° C. Especially, the invention provides a coffee pulp treatment process comprising: (a1) providing coffee pulp, obtainable from a production process for producing green coffee beans from coffee cherries; (a2) subjecting the coffee pulp to a preservation process comprising: (a2a) combining the coffee pulp with a preservation liquid comprising a sulfite and a divalent cation and bringing the pH of the thus obtained mixture at 4 or lower; (a2b) optionally heating the mixture to a temperature of at least 60° C.; and (a2c) removing liquid from the (thus obtained) mixture.

It appears that with such process, especially including the heating stage, allows preservation of the coffee pulp for a at least a year, such as for shipping the pulp to another site for pectin extraction. The above process thus provides coffee pulp that can safely be stored, without substantial deterioration. Either directly after production of the pulp, or after the storage process, the extraction, especially the acid extraction may take place, as defined herein.

In an embodiment, fresh coffee pulp (also indicated as husk) obtained e.g. from the wet mill of coffee cherries, is processed by collecting the material and combining with a preservation liquid. Especially, at least two preservation liquids are used, wherein the first may have a neutral pH, such as 6-8, especially 6.5-7.5, and may comprise ions like calcium, and sulfite, and wherein the second preservation liquid is an acid liquid, which may mainly be used to lower the pH of the mixture. These two liquids may be added in two stages. Optionally, only a single preservation liquid may be applied, including e.g. the above indicated elements and having an acid pH. The first preservation liquid may thus be applied first; the second liquid may be applied thereafter, see also below.

Especially assuming a multi-stage process with two preservations liquids, first the first preservation liquid (herein also indicated as "PS1)" is applied. The coffee pulp and preservation liquid may be combined in a volume ratio from 1:0.5-1:10, especially 1:1-1:5 (such as a 1:3 volumes liquid to pulp ratio). A good mixing and/or a complete coverage with the preservation liquid is desirable. Especially, the pulp is submerged in the (first) preservation liquid. Mixing and an optional subsequent period without mixing may especially take in the range of 1-100 hours (though longer may also be possible), such as in the range of 3-72 hours, like in the range of 6-24 hours. This may provide the desired intimate contact between the preservation liquid and the coffee pulp.

The (first) preservation liquid is especially an aqueous liquid. Further, the preservation liquid especially comprises one or more of a calcium salt and a sulfite salt (especially is dissolved state, i.e. it comprises one or more of calcium cations and sulfite anions). In an embodiment, the preservation liquid comprises one or more of a sulfite anion $SO_2^{2-}$ (hyposulfite), $SO_3^{2-}$, $HSO_3^-$, (bisulfite ion), $S_2O_5^{2-}$ (metabisulfite ion), $SO_5^{2-}$ (persulfate ion), $SO_4^{2-}$ (sulfate ion), $SO_2^{2-}$ (hyposulfite ion), $S_2O_3^{2-}$ (thiosulfate ion). Salts that may be used are e.g. selected from the group consisting of sodium sulfite ($Na_2SO_2$), sodium bisulfite ($NaHSO_3$), sodium metabisulfite ($Na_2S_2O_5$), potassium sulfite ($K_2SO_2$), amongst others. $SO_2$ may also be used, which upon introduction into water may provide sulfite, especially under alkaline conditions. Sulfite antibrowning may be based on an inhibition of enzymatic activity or formation of colorless adducts with enzymatically formed o-quinones. Surprisingly, at the same time the sulfite compound appears to have an antimicrobial inhibition effect in fungal growth. Furthermore, to maintain integrity of the cellular wall and reduce dissolution of valuable compounds from the coffee pulp/husk, it may be advantageous to include a divalent cation in the preservation liquid. By adding divalent cations the soluble pectin becomes insoluble. To this end, divalent cation salts such as calcium chloride ($CaCl_2$) and/or magnesium chloride ($MgCl_2$). Especially the divalent cation comprises an alkaline earth cation. It appears that the divalent cation may keep the pectin and the other compounds that are valuable ingredients insoluble. A sulfite salt, such as sodium bisulfite, may be available in preservation liquid the range of 0.01-5 wt. %, such as 0.1-2 wt. %. The cation salt, such as calcium chloride, may be available in the preservation liquid in the range of 0.1-10 wt. %, such as 0.1-1 wt. %. Further, the preservation liquid ascorbic acid and/or an ascorbate, such as sodium ascorbate. Alternative to ascorbic acid and/or ascorbate, or additional to it, also one or more of sodium citrate and potassium citrate ma be applied.

The pH of the mixture is about in the range of about 6-7 and may be brought at a pH of 4 or lower, such as 3.5 or lower. Especially the lowering of the pH is only done after the above indicated period of mixing and the optional subsequent period without mixing (with the first preservation liquid) (amongst others the above indicated 1-100 hours). Acidification may be done with a second liquid (herein also indicated as PS2 or second preservation liquid) comprising an acid, especially an organic acid. The second liquid may comprise one or more acids selected from the group consisting of citric acid, lactic acid, nitric acid, sulfuric acid, phosphoric acid, hydrogen chloride, among others. Further, optionally EDTA may be added as preserving agent. Alternative to or in addition to EDTA, also one or more of cysteine, glycine, methionine and other amino acids may be applied. Hence, in an embodiment the preservation liquid comprises a calcium salt and sodium ascorbate, and the pH (of the mixture of the first preservation liquid and the coffee pulp) is brought at 3 or lower with a liquid comprising an organic acid, and wherein optionally EDTA is added to the mixture (i.e. the second preservation liquid). EDTA, and/or one of the other alternatives may be contained in the second preservation liquid or may be added separately to the mixture (of the first preservation liquid and the coffee pulp (and the second preservation liquid). The (second) preservation liquid is (also) especially an aqueous liquid.

Especially, the pH of the mixture is lowered to 4 or lower, especially 3.5 or lower, even more especially 3 or lower, or a pH of 2 or lower. The second liquid and the mixture will be mixed with each other. Optionally, the first liquid is at least partly removed (before the second liquid is added). However, also the mixture, including the first liquid, may be used and brought at the desired pH.

Thereafter, the thus obtained mixtured may kept, optionally while mixing, for a period of at least 15 minutes, such as at least 30 minutes, such as in the range of 0.5-3 hours. Hence, the entire stage of mixing with the second liquid and optional subsequent period without mixing may be in the range of 0.5-10 hours, especially 0.5-5 hours.

During the first period with the first liquid and/or during the second period with the second liquid, the mixture may be heated. Especially however, these stages are executed at ambient temperatures, or temperatures below at least 40° C., but above the freezing point of course. After the acidification, and the optional rest stage (such as the period of the 0.5-5 hours, the thus obtained mixture is especially brought at an elevated temperature of at least 60° C., especially at least 70° C. The mixture may be kept at this temperature for at least 5 minutes, such as in the range of 5 minutes-2 hours, like 5-60 minutes, such as 10-60 minutes. Hence, the process may also include a stage wherein the mixture is heated to a temperature of at least 70° C. for at least 5 minutes. Especially, the temperature is not increased over 95° C., such as at maximum 90° C. By heating, at least part of the (aqueous) liquid is removed. This facilitates further processing, such as a pressure stage. Also, enzymes that might otherwise deteriorate the pectin are inactivated by the elevated temperature.

Thereafter, the liquid is removed. This may include a drying step at elevated temperatures and/or a sun-based drying. Especially, however, a pressure stage is included wherein at least part of the liquid is removed. Optionally, the stage of applying pressure to the mixture may also include forming larger conglomerates, such as pellets or briquettes. The pressure stage may include applying a pressure to the mixture in the range of 2-50 bar, such as 5-20 bar in which at least part of the liquid is drained from the mixture of coffee pulp and preservation liquid. The coffee pulp may optionally be further dried, e.g. by sun drying or by mechanical drying. The drained liquid can be optionally recirculated. Optionally, before the pressure stage, liquid may be partly drained off.

An alternative to the physical stress and drying is the use of a pelletizer for the biomass at high temperatures. In this case the pulp may be drained from excess of water leaving the material with a water content between 5-50% of water on dry basis (optimum 15% water content). The drained coffee pulp is then added to the pelletizer machine working at a temperature of between 70-90° C. (optimum is 80° C.) which transforms the biomass in pellets of 5 mm diameter.

An alternative to the heating and physical stress is the extrusion of the coffee pulp. The extrusion process may especially include the use of an (commercial) extruder such as biomass briquetters or pelletizer machines working at lower temperatures than the normal (between 120-180° C.) and pressures ranging between 10-150 bar (optimum 50 bar).

Hence, the process especially include removing at least part of the liquid after the preservation liquid(s) have been applied to the coffee pulp, such as by heating, or by other methods known in the art, followed by an extrusion process, which extrusion process may optionally include a pelletizing stage or a briquetting stage, for forming pellets or briquets. In the extrusion stage, further liquid is removed from the mixture ("preserved coffee pulp"). Therefore, the liquid may be removed in a process comprising one or more of (i) heating the mixture (of the preservation liquid and the coffee pulp), (ii) pressing the liquid out of the mixture, (iii) pelletizing the mixture at a temperature of at least 50° C., (iv) extruding the mixture, or (iv) briquetting the mixture. Especially, the (liquid removal) process comprises (i) heating the mixture (of the preservation liquid and the coffee pulp), followed by extrusion, including one or more pelleting or briquetting. Hence, in an embodiment of the process, the liquid is removed in a process comprising one or more of (i) heating the mixture (of the preservation liquid and the coffee pulp), (ii) pressing the liquid out of the mixture, (iii) pelletizing the preserved coffee pulp at a temperature of at least 50° C., (iv) extruding the preserved coffee pulp, or (v) briquetting the preserved coffee pulp.

The invention also provides a coffee pulp treatment process comprising:
a1. Providing coffee pulp, obtainable from a production process for producing green coffee beans from coffee cherries;
a2: Subjecting the coffee pulp to a preservation process comprising:
  combining the coffee pulp with a preservation liquid comprising a sulfite and a divalent cation and bringing the pH of the thus obtained mixture at 4 or lower;
  optionally heating the mixture to a temperature of at least 60° C.;
  removing liquid from the mixture;
b. Extracting from the coffee pulp a pectin comprising extract, wherein extraction is performed under acid conditions or alkaline conditions, especially at least under acid conditions, to provide the pectin comprising extract.

The herein indicated stages of "optionally heating the mixture to a temperature of at least 60° C.; removing liquid from the mixture" especially refer to a stage wherein the liquid is removed from the mixture, which removal stage may optionally include a stage wherein the temperature is elevated. This facilitates removal of the liquid. The heating stage also appears to have beneficial effect on the preservation of the coffee pectin. Heating seems to inactivate enzymes that may otherwise degrade the pectin (see also above).

Instead of coffee pulp, also other pectin comprising agricultural by-products may be applied, especially pectin extracted from the industrial residues of cacao, palm oil, olive oil and sugar from beetroot (SBP). The invention is however further mainly elucidated with reference to coffee pulp and coffee pectin.

Hence, in a further aspect, the invention provides a coffee pulp treatment process comprising:

a. Providing coffee pulp, obtainable from a production process for producing green (i.e. non-roasted) coffee beans from coffee cherries; optionally subjecting the coffee pulp to the preservation process as described herein;
b. Extracting from the coffee pulp a pectin comprising extract, wherein extraction is performed under acid conditions or alkaline conditions (or one after the other), to provide (or produce) the pectin comprising extract, especially wherein the extraction comprises extracting from the coffee pulp a pectin comprising extract, wherein extraction is performed under (at least) acid conditions. Further, the process may include:
c. (optionally) enzymatic treatment of the pectin comprising extract, wherein the (optional) enzymatic treatment comprises a treatment with one or more enzymes selected from the group consisting of an esterase and/or a reductase, to provide an enzymatically treated (or modified) pectin material, especially polyphenol functionalized coffee pectin extract, especially wherein the enzymatic treatment comprises at least a treatment with an oxidoreductase; and
d. (optionally) extraction of polyphenol functionalized coffee pectin extract from the product of the (optionally) enzymatic treated pectin comprising extract (i.e. the product obtained at c).

With this process, advantageously in an embodiment (polyphenol functionalized) coffee pectin extract is produced, which is a product that can be used for several applications, and which leads to a remaining product that has a substantially reduced content in polyphenols, and may therefore be more easily reused or discarded as waste.

The coffee pulp that is used for the process may directly be obtained from a plant, but may also have been subjected to a conservation process, such as described herein. The coffee pulp used may also be obtained from a remote place (like >10 km, or even >100 km or even further), and after transportation be used as coffee pulp in the process of the invention. Before transportation, the coffee pulp may optionally be treated for conservational purposes.

The extraction per se, especially including an alkali and/or acidic procedure, see also below, is also an aspect of the invention. Especially, subsequently the enzymatic treatment is applied, which may be used to demethylate and/or cross-link. However, the product obtained after the extraction may also be used as such (see also below), e.g. as emulsifier. Experimentally, it was found that this emulsifier has much better properties than other emulsifiers (more stable emulsions), such as e.g. based on sugar beet pectin. A main difference between the pectin obtained after the acid and/or alkaline extraction, especially acid extraction, and the same but after the enzymatic treatment, is that in the former there are substantially no polyphenol cross-links between the pectin polymers, wherein in the latter these are available.

The term "green coffee bean" is known in the art and especially refers to the non-roasted coffee bean. The cherries that are used in de-pulping may be in a ripe or unripe state. Also mixtures of unripe and ripe cherries may be applied. The properties of the (polyphenol functionalized) coffee pectin extract may depend upon whether ripe and/or unripe coffee beans are applied.

Pectin can be extracted from multiple sources, however pectins are mostly extracted from citrus peels and apple pomace. As mentioned above, pectins are chemically and/or enzymatically modified to obtain desired gel structures. Another source of pectin that has been accepted is pectin extracted from the industrial residues of sugar from beetroot (SBP). Physicochemical differences between SBP and other type of conventional pectins include higher proportion of neutral sugar side chains, a higher content of acetyl groups at O2 and O3 positions within the galacturonic backbone and a higher content of phenolic esters in the side chains particularly in the arabinose and galactose, and a higher content of protinaceous materials bound to the side chains through covalent linkages. Unexpectedly, coffee pectin shares some of the characteristics intrinsic to SBP, the presence of important amounts of galactose and arabinose in the neutral side chain, and the presence of polyphenols among others. It is therefore theorized that coffee pectin can be modified as SBP and yield high value pectins with emulsifying characteristics. Also coffee pectin can be chemically modified as citrus peel pectin to produce the desired gel, in this aspect research and standardisation are still needed.

Instead of coffee pulp, also other pectin comprising agricultural by-products may be applied, especially pectin extracted from the industrial residues of cacao, palm oil, olive oil and sugar from beetroot (SBP). Hence, in another aspect, the invention provides a pectin comprising agricultural by-product treatment process comprising:
a. Providing a pectin comprising agricultural by-product;
b. Extracting from the pectin comprising agricultural by-product a pectin comprising extract, wherein extraction is performed under acid conditions or alkaline conditions (or one after the other), to provide the pectin comprising extract, especially wherein the extraction comprises extracting from the coffee pulp a pectin comprising extract, wherein extraction is performed under (at least) acid conditions;
c. (optionally) Enzymatic treatment of the pectin comprising extract, wherein the enzymatic treatment comprises a treatment with one or more enzymes selected from the group consisting of an esterase and a reductase, to provide a enzymatically treated pectin material, especially wherein the enzymatic treatment comprises at least a treatment with an oxidoreductase; and
d. (optionally) Extraction of polyphenol functionalized coffee pectin extract from the product of the optionally enzymatic treated pectin comprising extract.

The invention will further be elucidated with respect to (pectin comprising) coffee pulp.

In a specific embodiment, the coffee pulp is subjected to a first extraction under acid conditions, leading to a first extraction product and a residual product, wherein the residual product is further subjected to a second extraction under alkaline conditions, leading to a second extraction product and a second residual product, and wherein the from this second extraction obtained second extraction product is optionally recombined with the first extraction product from the first extraction, and wherein these optionally combined pectin extraction products are then further subjected to the enzymatic treatment. Especially, in the second extraction a second extraction liquid is applied that comprises $H_2O_2$. $H_2O_2$ may be used as oxidizing agent and/or as substrate for the enzyme(s). $H_2O_2$ may allow e.g. the reaction of a laccase and/or a peroxidase, especially a peroxidase, for cross linking. However, other oxidizing agent can be used (oxygen donors). Alternatively or additionally to $H_2O_2$ also ammonium persulfate $((NH_4)_2S_2O_8)$ and/or sodium metabisulfite $(Na_2S_2O_5)$ may be applied. Optionally or additionally, also ozone might be applied. The extraction may also include a separation step separating the extract from the remaining product, such as by filtration etc. (see also below).

The term "acidic conditions" and similar terms especially indicate a pH<7, especially ≤6; the term "alkaline" conditions and similar terms especially indicate a pH>7, especially ≥8.

As can be derived from the above, in an embodiment the method may include extracting (from the pectin comprising agricultural by-product) a pectin comprising extract, wherein extraction is performed under acid conditions to provide the pectin comprising extract, followed by the enzymatic treatment. The additional extraction under alkaline conditions is a specific embodiment. As can be derived from the above, also in an embodiment the method may include extracting (from the pectin comprising agricultural by-product) a pectin comprising extract, wherein extraction is performed under alkaline conditions, to provide the pectin comprising extract, followed by the enzymatic treatment. The additional extraction under acid conditions is a specific embodiment. The acid extraction process especially provides a pectin that is useful for the food industry. The (additional) (dilute) alkali extraction may assist in extracting pectin that has low solubility in water.

As can be derived from the above, in an embodiment the method may include extracting (from the pectin comprising agricultural by-product) a pectin comprising extract, wherein extraction is performed under acid conditions and alkaline conditions, to provide the pectin comprising extract which is a combination of the alkaline extraction product and acid extraction product, followed by the enzymatic treatment (of the combination of extracts). As will be discussed below, the acid extraction may be subsequent to the alkaline extraction or the alkaline extraction may be subsequent to the acid extraction. The phrase "wherein extraction is performed under acid conditions and alkaline conditions" in general indicates that first an extraction is performed under acid or alkaline conditions and that (subsequently) the remaining material from the acid or alkaline extraction is subjected to an alkaline or acid extraction, respectively. The extracts can be combined for further (enzymatic) processing and the remaining material can be used for other applications or discarded (see elsewhere herein).

In a preferred embodiment, the acid conditions of the first extraction are at a pH in the range of 0.5-4, especially 1.5-3. Further, the first extraction may especially be performed at a temperature of at least 80° C. The alkaline conditions in the second extraction are especially at a pH in the range of 7-14, such as 8-14, even more especially 7-11, such as 9-11, such as especially between 7.5-10.5, such as 9.5-10.5. For the alkaline extraction, the pH is >7, especially 7.5-9. At larger pH, the pectin molecule may start getting hydrolyzed. Further, especially the alkaline extraction is performed at a temperature not higher than 45° C. especially 35° C.

Further, in embodiments the one or more enzymes are selected from the group consisting of diphenol oxidoreductase, peroxidase, laccase, pectin-esterase, methyl-esterase, poly galacturanase, endo polyglucanase, and exo polyglucanase. Alternatively or additionally, one or more enzymes selected from the group consisting of pectin lyase, polygalacturonase (endo and exo), endo galactanase, exo galactanase, rhamnogalacturonase may be applied. Alternatively or additionally, especially arabinofuranosidase, arabinase, feruloyl esterase, endo pectin methyl esterase, exo pectin methyl esterase, pectin esterase, laccase, peroxidase (especially from horseradish) may be applied. For demethylation, especially enzymes like pectin methyl esterase (EC 3.1.1.11) can be applied. For cross-linking, especially enzymes like peroxidase (especially EC 1.10 or EC 1.11, such as e.g.

horseradish peroxidase 1.11.1.7) may be applied. Especially, the enzymatic treatment at least involves a treatment of the extract(s) with an oxidoreductase. An oxidoreductase is an enzyme that catalyzes the transfer of electrons from one molecule (reductant or electron donor) to another the molecule (oxidant or electron acceptor). Best results are obtained with an oxidoreductase selected from the (sub) classes EC 1.10 (oxidoreductases that act on diphenols and related substances as donors) and EC 1.11 (oxidoreductases that act on peroxide as an acceptor (peroxidases)). Especially good results were obtained with horseradish peroxidase (1.11.1.7) and laccase (EC 1.10.3.2). The former may need $H_2O_2$ whereas the latter may use dissolved oxygen and may not necessarily need an additional oxygen donor. Hence, especially the enzymatic treatment comprises at least a treatment (of the pectin comprising extract) with one or more enzymes selected from the group consisting of EC 1.10 or EC 1.11. The EC 1.10 class enzymes (or enzymatic reactions) are acting on diphenols and related substances as donors, with e.g. NAD+, NADP+, cytochrome, oxygen, copper or other acceptors. Especially those with oxygen as acceptor are used. The EC 1.11 class enzymes (or enzymatic reactions) are acting on peroxide as acceptors. Here, as will be known to the person skilled in the art, the international accepted enzyme nomenclature, such as especially defined by the Nomenclature Committee of the International Union of Biochemistry and Molecular Biology (NC-IUBMB), is applied.

However, the process may also be performed in an alternative way, wherein the alkaline and acid extraction order is reversed. Hence, in yet another embodiment, the coffee pulp is subjected to a first extraction under alkaline conditions, leading to a first extraction product and a residual product, wherein the residual product is further subjected to a second extraction under acid conditions, leading to a second extraction product and a second residual product, and wherein the from this second extraction obtained second extraction product is optionally recombined with the first extraction product from the first extraction, and wherein these optionally combined pectin extraction products are then further subjected to the enzymatic treatment. Especially, during the first extraction a first extraction liquid is applied that comprises $H_2O_2$. As indicated above, $H_2O_2$ may be used as oxygen donor and/or as substrate for the enzyme(s). In a preferred embodiment, the alkaline conditions on the first extraction are especially at a pH in the range of 7-14, such as 8-14, especially 7-11, such as 9-11, more especially 7.5-10.5, such as 9.5-10.5. For the alkaline extraction, the pH is >7, especially 7.5-9. At larger pH, the pectin molecule may start getting hydrolyzed. Further, especially the alkaline extraction is performed at a temperature not higher than 45° C. especially 35° C. Further, especially the acid conditions of the second extraction are at a pH in the range of 0.5-4, especially 1.5-3. In further embodiments, the second extraction is especially performed at a temperature of at least 80° C.

The enzyme may be used in one or more of the following instances: during the acid extraction, after the acid extraction, during the alkaline extraction, after the alkaline extraction, and during a stage when both extracts have been combined. Of course, during one or more of these stages, an enzyme may be applied. Especially, the enzyme, and optional additive for the enzyme such as $H_2O_2$, may depend upon the pH and/or temperature. $H_2O_2$ may for instance only be applied when peroxidase is used, especially horse radish peroxidase. Laccase does not need $H_2O_2$ to generate the polyphenol cross-links. However, laccase in general only substantially acts at pH between about 6.0-8.5. Horse radish peroxidase acts in general only substantially at pH higher between about 8.5-12.5. The extraction pH may thus e.g. also depends in the enzyme used, though, if necessary, after extraction the pH may also be altered to arrive at a pH suitable for the chosen enzymes. Therefore, in embodiments wherein (horse radish) peroxidase is applied, the presence of $H_2O_2$ is desired and the pH range, during at least part of the process, is especially from 6.0-11 since this the range where the reductase is more active. The temperature in the alkali extraction is especially not over 45° C. Further, the optimum temperature for both laccase and peroxidase is in the range of 30-40° C., such as about 35° C. Enzymes may be added during any stage of the process, but are of course at least available during the enzymatic treatment.

Yet in further embodiments, the one or more enzymes are especially selected from the group consisting of diphenol oxidoreductase, peroxidase, laccase, pectin-esterase, methyl-esterase, poly galacturanase, endo polyglucanase, and exo polyglucanase. Alternatively or additionally, one or more enzymes are selected from the group consisting of pectin lyase, polygalacturonase (endo and exo), endo galactanase, exo galactanase, rhamnogalacturonase may be applied. Alternatively or additionally, especially arabinofuranosidase, arabinase, feruloyl esterase, endo pectin methyl esterase, exo pectin methyl esterase, pectin esterase, laccase, peroxidase (especially from horseradish) may be applied. For demethylation, especially enzymes like pectinesterase can be applied. For cross-linking, especially enzymes like peroxidases may be applied. As indicated above, during the enzymatic treatment especially at least an oxidoreductase selected from the (sub)classes EC 1.10 and EC 1.11 is applied. Note that the term "an enzyme" or "an oxidoreductases" and similar terms may also refer to a plurality of (different) enzymes or a plurality of (different) oxidoreductases, etc., respectively. As indicated herein, the enzymatic treatment may for instance be during an extraction stage or subsequent to an extraction stage, or multiple enzymatic treatments may be applied. Further, also a cocktail of different enzymes may be added. Assuming a oxidoreductases, the amount of enzyme used will be in the range of about 0.5-10 mg, such as especially about 1 mg of pure enzyme (100% protein) per 100 ml and assuming an esterase, the amount of enzyme used will be in the range of about 1-10 mg, especially about 5 mg of pure enzyme (100% protein) per 100 ml Hence, the enzymatic modification may be executed in a reactor, where there is an actual transformation of the matter. In one or more of the alkali and acid extraction there may be no (enzymatic) modification. Therefore, these may be executed in an extraction unit. During the enzymatic modification step the enzyme(s) may especially transform the pectin to a cross-linked pectin and/or may cleave groups attached to the pectin (macromolecules).

In a further specific embodiment, prior to the (first) extraction, the coffee pulp is subjected to a washing process, wherein the washing process comprises mixing the coffee pulp with a solvent and subsequently removing at least part of the solvent, wherein the water content of the solvent is ≤80 wt. %. Especially, at least 50 wt. %, even more especially at least 80 wt. %, of the solvent consists of one or more liquids having a polarity lower than water (vide infra).

In an embodiment, the extraction of (polyphenol functionalized) coffee pectin extract from the product of the optionally enzymatic treated pectin comprising extract comprises mixing at least part of the enzymatically treated material with an extraction liquid and subsequently removing at least part of the (polyphenol functionalized) coffee pectin, wherein the extraction liquid has a pH in the range of 3.5-6, such as 4-6. Especially, the extraction liquid comprises ethanol. However, the extraction liquid may also comprise other solvents, such as methanol, 2-propanol, acetone. The same type of solvent may be used as used for the washing process (see also below). Further, the extraction liquid may be acidified. Further, the extraction liquid may comprise a combination of two or more of (such) solvents. This extraction liquid may be used to precipitate the functionalized pectin. By adding the solvent, pectin may precipitate creating a gel which can be separated from the low molecular weight compounds dissolved in the solvent.

With the process of the invention, but optionally via other routes, a (polyphenol functionalized) coffee pectin extract may be obtained. Hence, in a further aspect, the invention also provides a (polyphenol functionalized) coffe pectin (per se), especially a (polyphenol functionalized) coffee pectin. Hence, especially the invention provides a (polyphenol functionalized) coffee pectin obtainable by the process as described herein. Especially, the polyphenol functionalized coffee pectin has a molar ratio of phenolic groups to the sum of arabinose plus galactose units between 20% to 60%, and has a molecular weight>90,000 Da, such as in the range of 90,000-200,000. In the pectin (product) of the invention, the protein content may be in the range of 5-18 wt. %, especially 8-15 wt. %. Further, the polyphenol content may be in the range of 0.06-0.18 wt. %, especially 0.09-0.15 wt. %. As known in the art, the protein content can be determined based on the Dumas method (ISO 16634-1:2008); the polyphenol content can be determined based on the Folin-Ciocalteu (ISO 14502-1:2005) method with the Folin-Ciocalteu reagent (FCR) or Folin's phenol reagent or Folin-Denis reagent, also called the Gallic Acid Equivalence method (GAE). This reagent (method) is especially designed for determining the phenol amount. Especially, the invention further provides a (polyphenol functionalized) coffee pectin (as described herein), having a molar weight<200,000 Da, such as especially <120,000 Da, such as in the range of 90,000-120,000 Da. The coffee pectin may have a total sugar content of rhamnose, arabinose, xylose, mannose, galactose, glucose, galacturonic acid, relative to the total sugar content, in the range of 70-95 wt. %, with a total galacturonic acid content, relative to the total sugar content, in the range of 55 to 80 wt. %. Further, the total glucose content, relative to the total sugar content, may be in the range of 3-15 wt. %. The total sugar content in the pectin (product) of the invention may be in the range of 40-80 wt. %, relative to the total weight of the product. The remaining part may include amongst others polyphenol and protein. Further, especially the Gal/UA ratio may be in the range of 0.1-0.2 (galactose-uronic acid weight ratio). Extracted citrus pectin may e.g. have a molecular weight that is much smaller, such as <70,000 Da.

Hence, the invention further provides a polyphenol functionalized pectin obtained (or obtainable) by enzymatic treatment of a pectin comprising extract from coffee pulp, wherein the enzymatic treatment comprises a treatment with one or more enzymes selected from the group consisting of an esterase and a reductase (and wherein the enzymatic treatment especially comprises at least a treatment with an oxidoreductases).

In addition to the above, further (intermediate) process steps may be included, such as one or more of precipitation, filtration, washing and resuspension. For instance, after recombination of the two extracts (or after acid extraction, but) before an enzymatic treatment, (also) a precipitation, filtration, washing and resuspension may take place. The terms "upstream" and "downstream" relate here to an arrangement of items or features, or a sequence of stages, relative to the propagation of a process chain, wherein relative to a first stage within a chain of process actions or process apparatus or process stages, a second stage in the process chain closer to the beginning of the chain is "upstream", and a third stage within the process chain further away from the process beginning is "downstream".

The coffee pectin is also of interest without the enzymatic treatment. In such instance, coffee pectins are obtained without the cross-links between the pectins (or pectin chains). Especially, the coffee pectins obtainable after ultrafiltration is of interest. The coffee pectin obtained with the present process including especially the preservation process and at least the acid extraction provides a coffee pectin that can be used very well as emulsifier.

Hence, in a specific embodiment, the coffee pulp treatment process as defined herein is used, wherein after one or more of extraction under acid conditions and alkaline conditions, especially at least acid extraction, the extraction process further comprises membrane ultrafiltration, wherein especially the membrane has a cut-off selected from the range of 50,000-150,000 Da, to provide the pectin comprising extract as permeate, wherein the pectin comprising extract after extraction under acid conditions and alkaline conditions but before membrane ultrafiltration is brought at a pH below 4, especially below 3.5 and optionally at a temperature selected from the range of 40-80° C. The membrane especially has a cut-off of 50,000 Da or larger, but especially not larger than 150,000 Da. A pH below 4, especially below 3.5 appears to prevent fouling of the membrane. Elevated temperatures are not necessary, but may decrease the filtration time. After the ultrafiltration, especially one or more diafiltrations are applied (especially with the same cut-off type of membrane). Thereafter, a washing with e.g. water may be applied.

In this way, the invention also provides a coffee pectin, having a molecular weight>50,000 Da, having a degree of methylation (DM) of >75% and a degree of acetylation (DAc)>75%, wherein the protein content is in the range of 5-18 wt. % and wherein the polyphenol content is in the range of 0.01 wt. % or less. Especially, a coffee pectin is provided having a molar weight in the range of 50,000-120,000 Da, having a total sugar content of rhamnose, arabinose, xylose, mannose, galactose, glucose, galacturonic acid, relative to the total sugar content, in the range of 70-95 wt. %, with a total galacturonic acid content, relative to the total sugar content, in the range of 55 to 80 wt. %, and having a total glucose content, relative to the total sugar content, in the range of 3-15 wt. %, wherein the polyphenol content is in the range of 0.01 wt. % or less. This coffee pectin may be used as emulsifier. For instance, coffee pectins may be provided having a molar weight of >80,000 Da, or even >90,000 Da, like >100,000 Da, which may have excellent gelling properties. In yet a further process, the invention thus also provides a coffee pulp treatment process comprising:

a. Providing coffee pulp, obtainable from a production process for producing green coffee beans from coffee cherries;

b. Extracting from the coffee pulp a pectin comprising extract, wherein extraction is performed under acid conditions or alkaline conditions, to provide the pectin comprising extract;

c wherein after one or more of extraction under acid conditions and alkaline conditions, the extraction process further comprises membrane ultrafiltration, wherein especially the membrane has a cut-off selected from the range of 50,000-150,000 Da, to provide the pectin comprising extract as permeate, wherein the pectin comprising extract after extraction under acid conditions and alkaline conditions but before membrane ultrafiltration is brought at a pH below 4, especially below 3.5 and optionally at a temperature selected from the range of 40-80° C.

Optionally, the process may also include the above described preservation process, i.e.:

a2: Subjecting the (thus provided) coffee pulp to a preservation process comprising:
 combining the coffee pulp with a preservation liquid comprising a sulfite and a divalent cation and bringing the pH of the thus obtained mixture at 4 or lower;
 optionally heating the mixture to a temperature of at least 60° C.;
 removing liquid from the mixture.

The term "substantially" herein, such as in "substantially all emission" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The apparatus herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to an apparatus comprising one or more of the characterizing features described in the description and/or shown in the attached drawings. The invention further pertains to a method or process comprising one or more of the characterising features described in the description and/or shown in the attached drawings.

Hence, the invention provides a treatment process wherein coffee pulp is used, after an option preservation, to extract from the coffee pulp in an extraction process, especially under acid conditions, pectin from the coffee pulp. With a process including ultrafiltration, with especially followed by diafiltration, a pectin is provided with excellent gelling properties. However, the process may also include an enzymatic treatment of the pecti obtainable after the extraction under especially acid conditions, which may provide the polyphenol functionalized pectin, which also has very interesting properties as gellant or emulsifier. The processes described herein provide a good use of coffee pulp and reduces environmental pressure.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1:
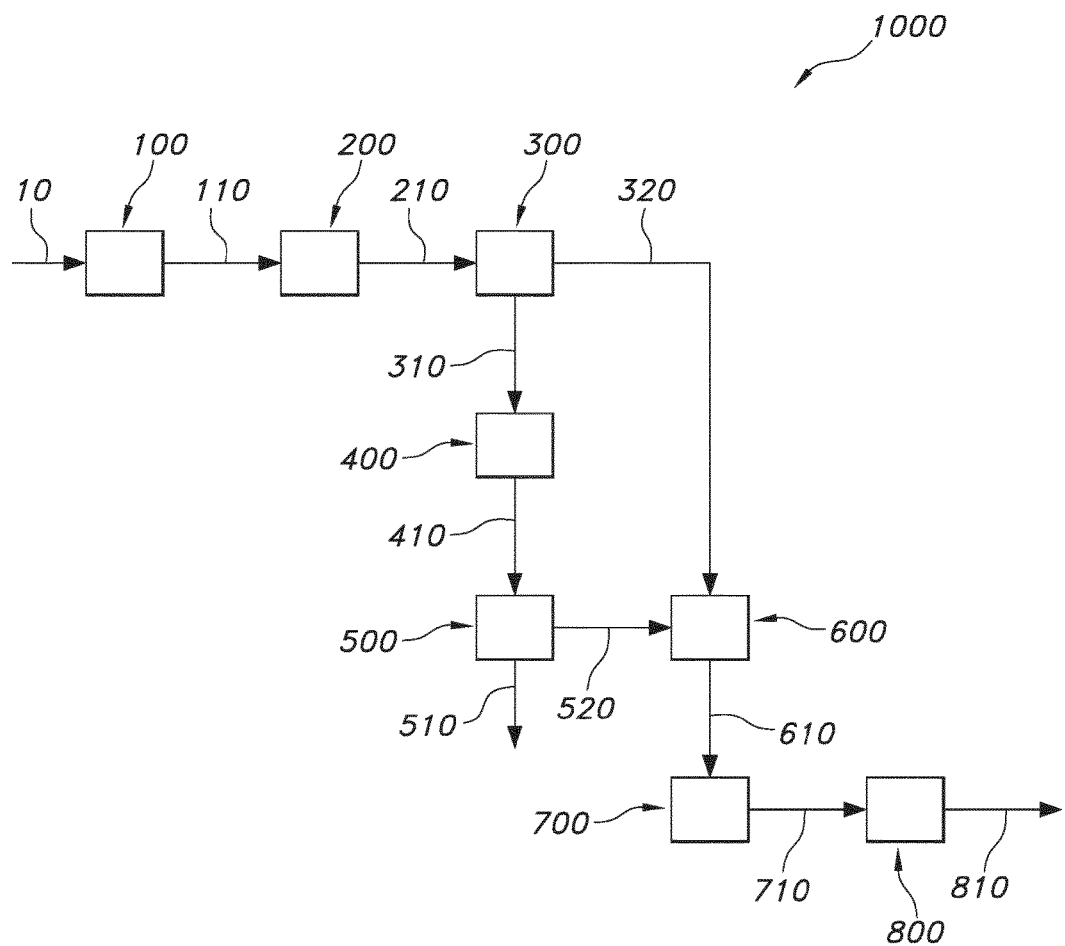
FIG. 1 schematically depicts an embodiment of the process as described herein.

FIG. 1 schematically depicts an embodiment of the process as described herein. Blended coffee pulp: the coffee pulp may relate to one or more of the exocarp, outer mesocarp (the pulp itself), and the mesocarp (mucilage or parchment). The hull (also known as silver skin) is not taken into account (later during the process, hulling machines may be used to remove the parchment layer) from wet processed coffee. Pulping dry processed coffee refers to removing the entire dried husk—the exocarp, mesocarp & endocarp—of the dried cherries. Further, optionally polishing may take place; this is an optional process in which any silver skin that remains on the beans after pulping (optionally a polishing machine may be applied). The pulp is preferably collected from the depulping mills as soon as possible after generation of the pulp, preferably in the first 24 hours. Would this not be possible, it is preferred to use preservation steps to minimize pectin degradation due to enzymatic activity. The preservation steps can be but are not limited to: acidification of the pulp to a pH below 4, alkalinisation to a pH above 9, lowering of the water activity to aw=0.5 or less at temperatures below 60° C., inactivation of the endogenous enzymes by solvent addition, inactivation of the endogenous enzymes by boiling and/or cooling (cycles). Addition of one or more preservation agents selected from the group consisting of sodium meta bisulfite, ascorbic acid, ethylenediaminetetraacetic acid (EDTA) may also be applied. Examples of (further preservation agents are e.g. selected from the group consisting of ascorbic acid, citric acid, oxalic acid, sodium metabisulfite, potassium bisulfite, sulfur dioxide, glycine, methionine and EDTA, especially one or more of sodium metabisulfite, potassium bisulfite, and EDTA.

Hence, in embodiments of the process, prior to the extraction (but especially after washing) the pulp is subjected to a preservation process, wherein the preservation process comprises one or more of (i) adding a preservation agent to the pulp and (ii) drying the pulp. As indicated above, the preservation agent may comprise one or more of ascorbic acid, citric acid, oxalic acid, sodium metabisulfite, potassium bisulfite, sulfur dioxide, glycine, methionine and EDTA, especially one or more of sodium metabisulfite, potassium bisulfite, and EDTA, especially one or more of sodium metabisulfite and potassium bisulfite. Further, it is preferred that the pulp is milled (or macerated) to a suitable particle size (after preservation but) prior to any processing step or stage. A suitable particle size is in the range between 10 and 40, such as e.g. 18 mesh. The coffee pulp is indicated with reference 10. The use of milled pulp may lead to a better extraction than when using unmilled pulp.

The (optional) clean-up procedure, herein also indicated as washing process, indicated with reference 100, may comprise the treatment of the (blended) coffee pulp with a solvent of low polarity, it can be, but is not limited to one or more of acetic acid, acetone, acetonitrile, acetyl acetone, 2-aminoethanol, aniline, anisole, benzene, benzonitrile, benzyl alcohol, 1-butanol, 2-butanol, i-butanol, 2-butanone, t-butyl alcohol, carbon disulfide, carbon tetrachloride, chlorobenzene, chloroform, cyclohexane, cyclohexanol, cyclohexanone, di-n-butylphthalate, 1,1-dichloroethane, diethylene glycol, 1-Methoxy-2-(2-methoxyethoxy)-ethane (diglyme), dimethoxyethane (glyme), N,N-dimethyl aniline, dimethyl formamide (DMF), dimethyl phthalate, dimethyl sulfoxide (DMSO), dioxane, ethanol, ether, ethyl acetate, ethyl acetoacetate, ethyl benzoate, ethylene glycol, glycerin, heptane, 1-heptanol, hexane, 1-hexanol, methanol, methyl acetate, methyl t-butyl ether (MTBE), methylene chloride, 1-octanol, pentane, 1-pentanol, 2-pentanol, 3-pentanol, 2-pentanone, 3-pentanone, 1-propanol, 2-propanol, pyridine, tetrahydrofuran (THF), toluene, such as especially one or more of methanol, a methanol water mixture, hexane, toluene, ethylene glycol, ether, ethyl ether. The solvent may optionally be acidified. The pulp is mixed with the solvent, preferably in a counter current extractor. The hydrocinnamic acids as well as the free polyphenols are dissolved. In this stream there may also be a rich fraction of caffeine which in later stage can be purified, and might be a sub product of the pectin extraction. The product obtained after the washing process is indicated with reference 110. Washing with a solvent may remove free polyphenols and caffeine from the coffee pulp and it may also precipitate polysaccharides of higher degree of polymerization. Washing with solvent may remove as much free polyphenols as possible without removing the polysaccharides that have polyphenols in their functional groups. Bottom line is solvent of lower polarity such as ethanol and propanol, precipitate the pectin with polyphenols attached while solubilizing caffeine and polyphenols that are not attached to the pectin structure. This allows to later using enzymes such as laccase to selectively modify pectin with biphenolic groups without loosing too much enzyme polymerizing the high amount of polyphenols. The washing liquid for the pulp may especially comprise less than 70 wt. % water, especially less than 65 wt. % water, such as less than 55 wt. %, or even lower. The liquid(s) used for the extraction(s) especially have a higher water content than the washing liquid (for the pulp). For instance, the extraction liquid(s) may comprise more than 65 wt. %, especially more than 75 wt. %, even more especially at least 80 wt. %, such as at least 90 wt. %, like at least 95 wt. % water. Further, the liquid(s) used for the extraction(s) especially have a higher polarity than the washing liquid (for the pulp). In this way, free polyphenols and caffeine may be removed from the pulp by the washing liquid and by extraction with a polar solvent (especially an acid(ified) polar solvent) pectin may be extracted from the insoluble solids of the pulp. Further, as indicated above, the extraction liquid(s) especially has a pH<7 or a pH>7. Optionally, the extraction liquid(s) may also comprise a (solved) salt (see also below).

In a first extraction step or stage, indicated with reference 200, the biomass, especially the product obtained after the washing process, may in an embodiment, be acidified to a pH=4 or lower, especially a pH=2 or lower, with a concentrated acid such as but not limited to one or more of hydrochloric acid, nitric acid, phosphoric acid, acetic acid. Further, the mixture may be heated, such as to a temperature of at least 70° C. The pH is preferably lowered before the heating step or stage can be applied. The ratio of biomass to (extraction) liquid may especially be in the range of 0.25:1-1:0.25, especially 0.5:1-1:0.5, such as 1:1 (which means that for each kilogram of fresh pulp one liter of solution is necessary for the extraction). It is preferably to use a high concentrated buffer solution to mix the biomass and then adjust the pH. Possible salts solutions are (but not limited) to one or more of sodium mono basic phosphate ($NaH_2PO_4$), sodium nitrate, sodium acetate, and sodium chloride. Alternatively or additionally, ammonium and/or potassium salts may be applied. Of course, more than one salt may be applied. The concentration of the salts may range between 50-400 mM, such as especially 100 mM to 200 mM (for each salt individually). Extraction may e.g. be executed in an extraction vessel or a counter current extractor where liquids and solids are mixed together and mixed continuously. It is desirable that heating is performed as fast as possible. Therefore, pre heating of the extraction vessel may be advisable. The product obtained after the first extraction step or stage is indicated with reference 210.

It is preferred that the first separation step or stage, indicated with reference 300, is performed on the hot mix (obtained in the first extraction step or stage). It is desired to recover as much solution (i.e. filtrate or supernatant) as possible before continuing with the next step or stage. According to the setup and magnitude of the stream different types of separation units can be used. Examples are a frame separator, a plate separator, a sieve (separator) and a centrifuge (separator). The solid precipitating from a liquid is called a precipitate (residual product, or first residual product), or when compacted by a centrifuge, a pellet. The liquid remaining above the solid is in either case called the supernate or supernatant. Also filtration with a filter may be performed. Filtration may also include membrane separation. The process of passing a mixture through a filter is called filtration. The liquid produced after filtering, in general a suspension of a solid in a liquid, is called filtrate, while the solid remaining in the filter is called retentate, residue, or filtrand. The remaining liquid after the first separation, the supernatant or filtrate (here the first extraction product), goes to a reactor in which it may be mixed with the supernatant of a second separation step or stage. The precipitate, retentate, residue, sediment or filtrand (first residual product) must especially be composed of only solid matter as much as possible. At this point the (remaining) biomass should be approximately 50% to 75% of the starting mass (dry weight).

The products obtained after the first separation step or stage are indicated with references 310 and 320. Reference 310 refers to the product that is remaining after the first separation, such as a retentate, residue, or filtrand, sediment, etc. This product 310 (first residual product) is especially subjected to a second extraction 400, see also below. The (desired) product, indicated with reference 320, of the separation action, i.e. a filtrate or permeate, or supernatant, etc. (first extraction product) can be directly introduced in a first reactor 600 (or reaction stage), see also below. The pectin comprising (extract after separation), in this embodiment indicated with reference 320, is a liquid product (extraction liquid with extract)

In a second extraction step or stage, indicated with reference 400, the first extraction residual product 310 or biomass may be mixed with alkali to extract the more ramified polysaccharides as well as more esterified pectins, which comprised the coffee pulp. This may in an embodiment be done in several steps or stages. First with a(n extraction) liquid, especially water, the biomass is diluted until 50% of the total dilution is achieved. Thereafter, the pH may be adapted, e.g. with concentrated alkali (i.e. an alkali solution), to a value of especially at least 9, like e.g. 10. In an embodiment, after adding the alkali, hydrogen peroxide may be added up to especially a concentration of up to 7.5%, especially up to 5% of the starting biomass. In the last stage of this extraction, the volume is completed with water. Extraction may be executed in an extraction vessel, a extraction vessel may be composed of a recipient in adequate material, such as stainless steel 320, 316 or alloys that prevents rust. A recirculating pump may or may not be present depending of the operation if continues or batch. The extraction vessels must include a source of heat and mixing mechanism. Mixing should be promoted to obtain higher rates of delignification and hydrolysis of the esterified compounds attach to the pectins. The temperature of the extraction vessel is especially regulated to avoid breakdown of the biopolymer. A suitable temperature is in the range of 35-65° C. The alkali concentration (of the concentrated alkali solution) is especially approximately 6 molar to 8 molar. The alkali (solution) can be based on a solution of e.g. one or more of sodium hydroxide, potassium hydroxide, calcium carbonate, and ammonium acetate. The product (mixture) obtained after the second extraction step or stage is indicated with reference 410.

In a second separation step or stage the aim is especially to separate the solids (from the product (mixture) obtained after the second extraction), i.e. the second (extraction) residual product, which are mostly cellulose and lignin from the free polysaccharides that are in solution (second extraction product), if necessary the pH can be lowered to 7 or 8 before separation. A lowering of the pH may be controlled to (substantially) prevent gelation of the pectins, which may lead to a loss of the biopolymers with the retentate. The second separation step or stage is indicated with reference 500. According to the setup and magnitude of the stream different types of separation units can be used. Examples are a frame separator, a plate separator, a sieve (separator) and a centrifuge (separator). The (desired) product of the (second) separation action, i.e. a filtrate or permeate, or supernatant, etc. (i.e. the second extraction product), indicated with reference 520, can (also) directly introduced in a first reactor 600. The second (extraction) residual product, not indicated, can be discarded.

Note that in this schematically indicated process the second extraction stage 400 is downstream of the first reaction stage. Note however that the acid and alkaline extractions may also be performed in another order, i.e. the first reaction stage including an alkaline extraction and the second reaction stage including an acid extraction. The product obtained after alkaline and acid extraction (or acid an alkaline extraction), may also be relevant per se. However higher quality pectins may be obtained when also the enzymatic processing as defined herein is applied. Alkaline extraction may optionally be omitted, acid extraction however is especially desired.

In a first reactor (herein also indicated as reactor 600, both acid-extracted pectins and if present alkali-extracted pectins may be mixed. Mixing may be done in ways known to the person skilled in the art, like with an extruder or a stirrer. Hence, the first reactor may especially include one or more of an extruder and a stirrer. Due to the change of pH some pectins can gel. Hence, it is especially preferred to lower the pH (of the alkaline liquid) slowly to a point near neutrality, especially in the range of 6-8 pH, preferably between pH 6.5-7.0. As indicated above, optionally directly after acid extraction, the enzymatic treatment may be executed. In such instance, the pH of the separation product may be increased to a pH in the range of 6-8 preferably between pH 6.5-7.0.

In the first reactor, especially two types of enzymes, oxidoreductase and/or esterase, are applied separately or in combination. Oxidoreductase is added according to its activity, i.e. the necessary amount to react with the pectin polymer is added. Examples of the oxidoreductase are (but not limited) to: diphenol oxidoreductase, peroxidase, and laccase. Esterase, especially pectin esterase, is added to control the degree of methylation and esterification of the pectin. Example of the (esterase) enzymes are (but not limited) to: pectin-esterase, methyl-esterase, poly galacturanase, feruloyl esterase, arabinose, arabino furanosidase and endo and exo polyglucanase (see also above). As indicated above, at least an oxidoreducatase may be applied, even more especially in combination with an esterase (especially Pectinesterase (EC 3.1.1.11)). In addition to the enzyme(s) also one or more further additives may be added. As indicated above, the pH may be changed (if necessary) to approximately neutral. Also other enzymes than defined herein, having the same functionality may be applied.

The product obtained after processing in the first reactor, or after processing in this reaction stage, is indicated with reference 610. This product may be subjected to a next reaction stage, which is indicated with reference 700. Herein, references 600 and 700 may (also) refer to different reactors, respectively. However, these references may also refer to reaction stages, which may in an embodiment be performed consecutively in different reactors whereas heat source, pH control and thermostat are present or in the same reactor. Reference 700 may also refer herein to a second reactor (or vessel).

In a second reactor (indicated with reference 700), a solvent, such as ethanol, methanol, 2-propanol, acetone especially an acidified solvent, such as acidified ethanol (like ethanol+1% Acetic acid anhydrous) is added, especially in the ratio of 1:1-1:10, such as 1.2:1:6, like 1:4 extraction solution to (acidified) solvent, such as ethanol. The function of the solvent is especially to change the polarity of the solution so the pectin will precipitate creating a gel which can be separated from the low molecular weight compounds dissolved in the solvent. The mix is left for coagulation of the pectins and precipitation. It is preferred that the pH in this stage is lower than 6; however is not advisable to have a pH lower than 3. If necessary, the solvent (or extraction liquid) preferably has a concentration of alcohol of 70% or higher. In an embodiment, the (second) reactor is or comprises also a decanter. In this way, the upper layer of the solution can be disposed leading to much smaller volume for the last separation step or stage.

In a third separation step or stage, indicated with reference 800, the unrefined pectin, indicated with reference 710, is separated from the solvent(s), such as ethanol and other solvents used during the process. Due to the colloidal characteristics of the pectins, in an embodiment a centrifuge may be applied for separating the pectins from the solvent(s). The product thus obtained (here the retentate, filtrand or sedimentation, etc.) is indicated with reference 810, which comprises the polyphenol functionalized (coffee) pectin. The product for this reaction stage (or this reactor) is indicated with reference 810, and can be indicated as the third extraction product (which is a solid material). Again, reference 800 may also refer to a further reactor, a third reactor which must be constructed in resistant material such as stainless steel 316, and 320, fire proof and suitable to work with volatile solvents. However, references 700 and 800 may also refer to a reactor including a decanter.

If desired, the pectins thus obtained can further be refined to meet specification in different industries. For instance, higher molecular weight pectins can be obtained by further crosslinking with (purified) enzymes and/or gelling pectins can be de-esterified to meet different types of application in the food and beverage industries. Furthermore, pectin can be modified with arabinase and arabinofuranosidase to obtain specific emulsification properties.

As indicated above, optionally the enzymatic process is not executed, and the coffee pectin is extracted from the product of the acid and/or alkaline process. This may include an ultrafiltration process with a membrane (see further also below).

Figure 2A:
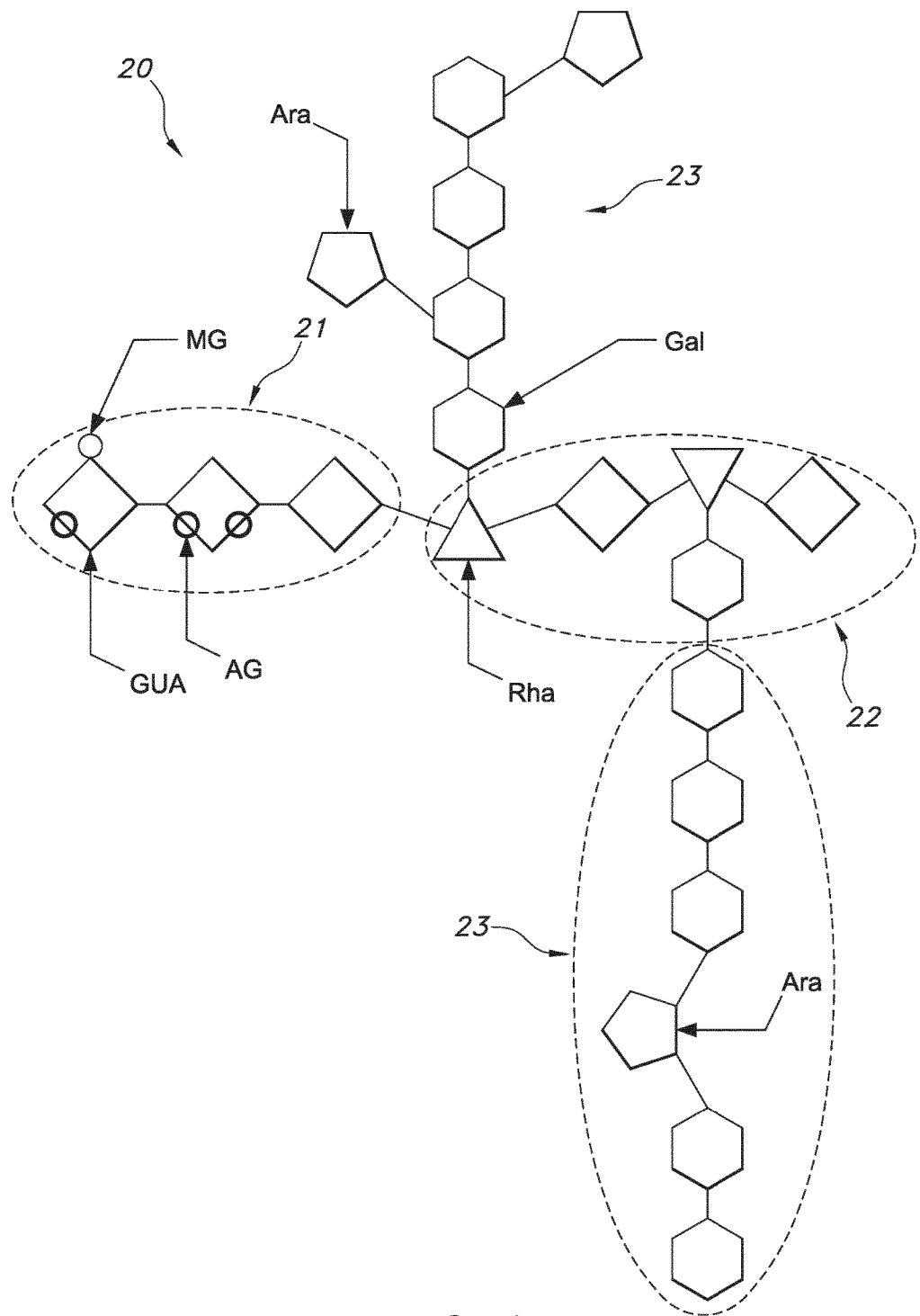
FIGS. 2a-2b schematically depicts coffee pectin (before and after processing as described in some embodiments herein)

A very schematic drawing of a pectin 20 from coffee pulp is indicated in FIG. 2a. MG refers to methyl group; AG refers to acetyl group, GUA refers to galacturonic acid, Gal refers to galactose, RHA refers to rhamnose, and Ara refers to arabinose. Reference 21 refers to the homogalacturonan region, reference 22 refers to a the rhamanogalacturonan I region, and reference 23 refers to the neutral side chain region of pectins.

Figure 2B:
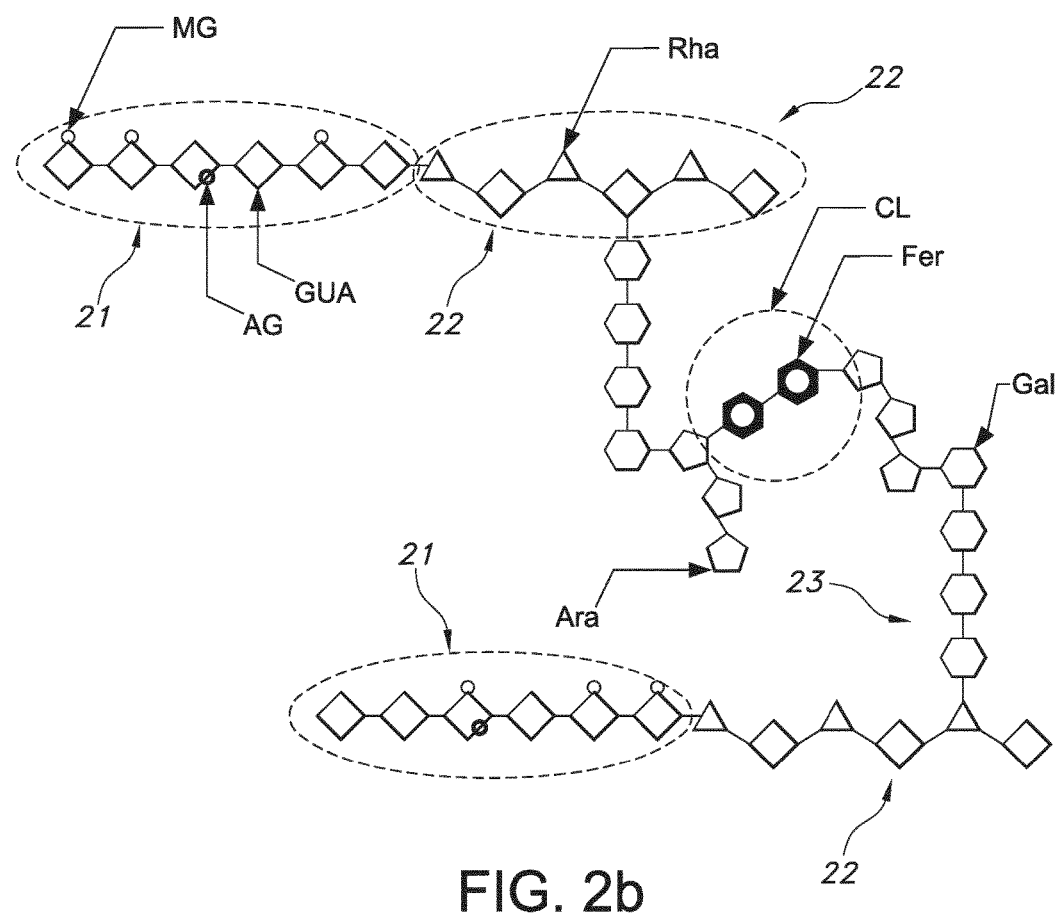

FIG. 2b very schematically depicts a pectin obtainable with the process of the invention, wherein the pectins are cross-linked via cross-link(s) CL. Reference Fer refers to ferulic acid (a phenol that is the basis of the cross-links, together with the arabinose units), of which of each pectin, via the arabinose units the pectins may be cross-linked with the aid of ferulic acid. The enzyme oxidoreductases, such as laccase and/or horse radish peroxidase, may generate cross-links in the form of polyphenols, such as diphenols or even polyphenols having more than two phenol groups. Coffee pectin obtainable after the alkaline and/or acid extraction, especially at least acid extraction, but before the optional enzymatic treatment does substantially not show the polyphenol cross-links CL between the pectins. Such cross-links may be available in less then 5% of all pectin chains ("heteropolysaccharide chains"), even more especially less than 1% of all pectin chains, especially substantially absent.

EXPERIMENTAL

Example 1

Extraction and modification of pectin from coffee pulp
Laboratory scale procedure:
Fresh pulp was obtained directly from a farm in Colombia in the beginning of January 2012. The cherries were in optimum ripe state to be separated from the bean in the wet mill. After the recollection the skin and pulp (exocarp and meso carp) were separated with a manual. The pulp, skin (pulp) are blended and freeze dried for transport to The Netherlands. 1 g of freeze dried material is washed 3 times with acidified ethanol 80% and centrifuge at 3000 rpm for 5 min in each step, the solids are then suspended in water, the pH is adjusted to 2.0 with hydrochloric acid and fill to 50 ml volume. The suspension is shaken in a water bath at 70° C. for 3 h. The suspension is then centrifuged at 3000 RPM for 10 min and the aqueous phase is separated from the solids. The solids are then neutralized and Sodium hydroxide is added to adjust pH at 10 and a final volume of 50 ml. The solids are suspended and shaken for 1 h at room temperature. After the alkali extraction the suspension is centrifuged at 3000 RPM for 10 minutes and the aqueous phase is pooled with the acid solution. The pH is adjusted to 6.0 with diluted alkali or acid. The spent material is then dried for further analysis. The liquid obtained for extraction has a brownish colour. 3 ml of Hydrogen peroxide is (30%) is added to the liquor and 500 ul of horse radish peroxidase solution (5 mg/ml) is added and the solution is stirred for 24 hours at room temperature. After the incubation 4 volumes of absolute ethanol are added and the pectin is left to precipitate for 2 hour at 4° C. After precipitation the suspension is filtered through a Whatman #3 filter paper with the aid of a Buchner funnel. The retenate solids are washed with 100 ml of acetone and dried at 50° C. for 12 h with high convection. The resulting film is then milled in a ball mill and stored for further analysis.

Example 2

The following procedure for obtaining soluble polysaccharides from coffee pulp, with certain degree of polymerization here after called pectin, this procedure is intended as a guide. Therefore modifications can of course be chosen. Materials: Coffee pulp (including coffee pectin): Coffee pulp from the variety *Coffea Arabica* was obtained fresh (coffee cherries were purchased directly from a farm in Colombia from the harvest of December 2011); Peroxidase from horseradish: Peroxidase from horseradish (HRP) was purchased from Sigma Aldrich EC 1.11.1.7 200 U/mg, Hydrochloric acid, sodium dihydrogen phosphate and sodium hydroxide of analytical grade were purchased from Merck Dramstad Germany.

Method: The coffee cherries were washed with water and the pulp was removed from the beans and parchments manually. The pulp was immediately macerated in a conventional blender at high speed and freeze-dried.

Clean Up Procedure (Washing Procedure):

1 g of coffee pulp was washed three times with a mixture of methanol water 50/50 (% v/v) and centrifuge, the supernatants were pooled and dried under vacuum at low temperature the retentate goes to the extraction procedure.

Acid Extraction:

The retentate was then suspended in 35 ml of water, the pH of the solution was adjusted to 2.0 by adding drop wise hydrochloric acid 6M and the final volume adjust to 50 ml. The mix was left in a shaking water bath at 90° C. for 1 h with continuous shaking and cool after to room temperature with cold water. The suspension was centrifuge at 3500 rpm.

Alkali Extraction:

The supernatant (first extraction product) is reserved (for later application, see below) and the retentate (residual product of the first extraction) is suspended in 25 ml of water. The pH is adjust to 12 with sodium hydroxide 4M drop wise, 5 ml of hydrogen peroxide solution 30% is added, the final volume is adjusted to 50 ml and shaken for 1 h at room temperature. The suspension is centrifuged at 3500 rpm for 5 min and the supernatant (second extraction product) pooled with the acid extracted fraction (first extraction product).

Enzymatic Reaction:

The pooled solution pH's is adjusted to 7.5 using diluted sodium hydroxide. 5 mg of lyophilized enzyme (here laccase) is diluted in 1 ml of sodium dihydrogen phosphate buffer at pH 7.5 and added to the pooled solution. The solution is left to react for 24 h at 35° C. temperature and continuous stirring. After incubation, the solution is boiled in a water bath for ten minutes to inactivate the enzyme.

Precipitation and Drying:

To the final solution, 4 volumes of ethanol 96% are added and left for precipitation for 3 h at 4° C., then filtrated through a Whatman N° 2 cellulose filter paper in a Buchener funnel. The retentate is washed 3 times with 50 ml of acetone, filtered and dried at 50° C. over 12 h. The obtain pectin is milled in a Retsch ball mill for 3 minutes at maximum amplitude.

Cross linking of pectins through the ferulic groups which are attached to the arabinan residues in the highly branched part of the pectin structure of sugar beet pectins (SBP), is known in the art. However, this mechanism only explains the oxidative crosslinking of the hairy region of the polysaccharide. Coffee pulp contains mainly galacturonic acid (GAU) (in between 60%-70% of the soluble sugars) and only 10% of arabinan and only a small % of rhamnose. This leads to the conclusion that coffee pectin (coffee pectin) is in fact predominantly composed by homogalagturonan (HG) which is the smooth region of pectins, in comparison to SBP which is compose mostly of RGI which is the branched region of pectins. Therefore it is concluded that pectins from SBP and coffee pectin are different in molecular structure, however coffee pectin shows an increased viscosity when sodium sulphite solutions are added and also in high alkali conditions.

From laboratory analysis, it is known that there is a high amount of polyphenols attached to the cell wall material in coffee pulp. It appears that there are at least two kinds of polyphenols; the polyphenols bound to the cell wall polysaccharides and the free ones. The free ones are analysed as tannins and condensable tannins. The bound polyphenols are hydrolysed by alkali in the second extraction step or stage, possibly because of the cleavage of the 2-O or 3-O bond in the GAU back bone chain. However there is a clear reaction when peroxidase enzyme is added with the $H_2O_2$ substrate.

From this experiment is also possible to state that possible applications for the enzyme untreated pectin are also possible. In this case only alkali extraction will be needed to obtain a gelling pectin without any other type of functionality. It is clear from the HPSEC (High Pressure Size Exclusion Chromatography) that unmodified coffee pectin has comparable size as the commercial citrus pectin (DM, degree of methoxylation, 30%) despite the absence of gelling properties in coffee pectin. It is theorised that this is due to the high methyl and acetyl esterification pattern in the coffee pectin (DM 88%; DA, Degree of amidation, 100%). The esterification pattern is too high to allow polymer interactions in solution, and therefore nullifying the interactions necessary to produce gel systems. Modification with pectic methyl estereases enzymes could lead also to an increase of viscosity. In table 1a the sugar composition of the raw materials. (Rha: rhamnose, Ara: arabinose, Xyl: xylose, Man: mannose, Gal: galactose, Glc: glucose, GalA: galacturonic acid) is indicated in weight percentages.

Characterization of Pectin from Coffee Pulp Preliminary Results

TABLE 1a

Sugar composition of the raw materials. (Rha: rhamnose, Ara: arabinose, Xyl: xylose, Man: mannose, Gal: galactose, Glc: glucose, GalA: galacturonic acid)

| Sugar composition % | Rha | Ara | Xyl | Man | Gal | Glc | GalA | Total sugar |
|---|---|---|---|---|---|---|---|---|
| Coffee pulp Pectin | 1 | 5 | 1 | 1 | 4 | 3 | 28.11 | 43 |
| Parchement Pectin | 1 | 8 | 3 | 2 | 4 | 22 | 47.22 | 87 |
| Raw pectin Extract | 0 | 1 | 0 | 0 | 1 | 1 | 24.08 | 29 |

TABLE 1b

Mole ratios for structure determination (UA: uronic acid)

| Sample name | Rha/ UA | (Ara + Gal)/ Rha | Ara/ Gal | (Ara + Gal)/ UA | Gal/ UA |
|---|---|---|---|---|---|
| Coffee Pulp pectin | 0.03 | 10.84 | 1.47 | 0.37 | 0.15 |

TABLE 2

Degree of methylation and acetylation for pectin extrated from coffee pulp
Degree of methylation/acetylation

| Sample | mg/mg MetOH | mg/mg AcOH | mg/mg UA | DM | DA |
|---|---|---|---|---|---|
| Coffee pulp pectin | 4.85% | 8.82% | 0.26740 | 100% | 97% |

Coffee pulp present high contents of hydrolysable tannins, 3.17% in d.b. (dry basis) Tanins is a broad name for polyphenols attached to the cell wall material in plants, for coffee is present in the pectin structure as hydro cinnamic, chlorogenic, and caffeic acids which are polyphenols with antioxidant activities.

Figure 3:
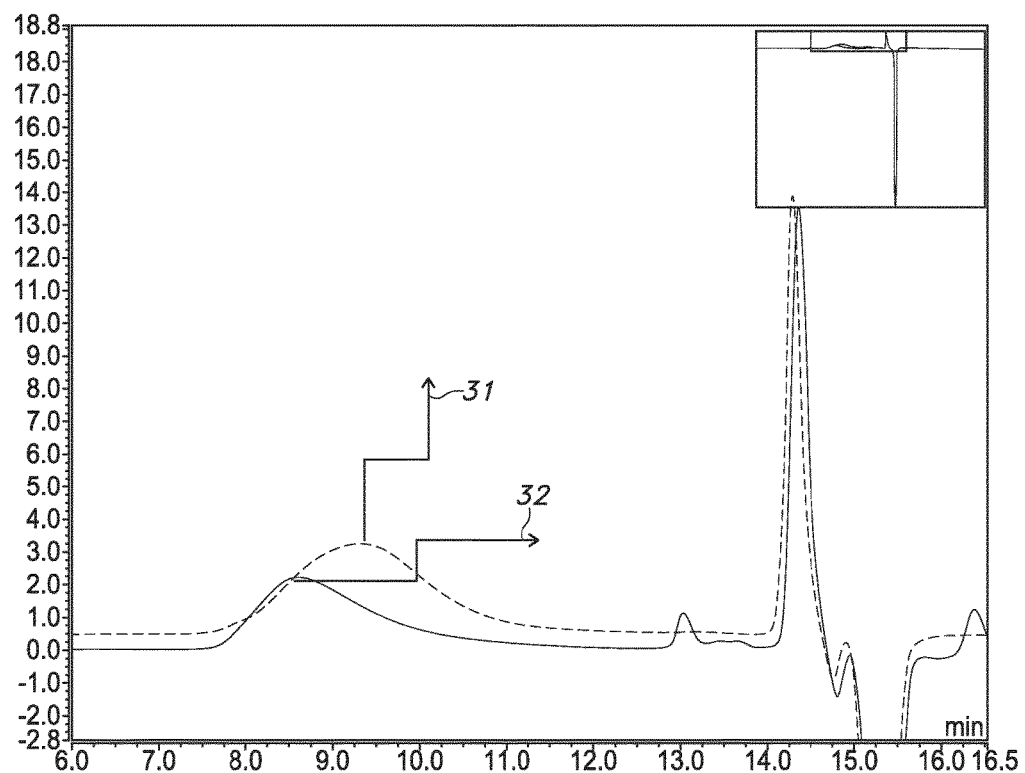
FIG. 3 shows a high performance size exclusion chromatography (HPSEC) for commercial pectin from citrus peel and pectin obtain with the herein described process.

There are examples in which polyphenols like ferulic acid, attach to the soluble part of the cell wall material through the arabinose residues. As can be seen in tables 1a-2 arabinose is present in a significant percentage in the coffee soluble pectin, and in the mucilage from the parchment fraction (parchment pectin). Therefore, the final pectin after the presently proposed process contains high amount of polyphenols. The ratio of phenolic groups to arabinose plus galactose will be between 20% to 60%, depending of the process yield. Commercial pectins that include phenolic groups are quiet rare, pectins extracted from sugar beet are an example of this type of pectins, however, pectins from sugar beet present higher degree of branching and lower amounts of galacturonic acid which cause the low gelling properties. The other main difference is the linearity of the coffee pectin molecule and molecular weight (>90,000 Da) which is close to the lemon pectin (120,000 Da to 160,000 Da) and not to the sugar beet pectin (that is in the range 50,000 Da to 80,000 Da), as can be seen in the HPSEC (high performance size exclusion chromatography) FIG. 3.

Figure 4:
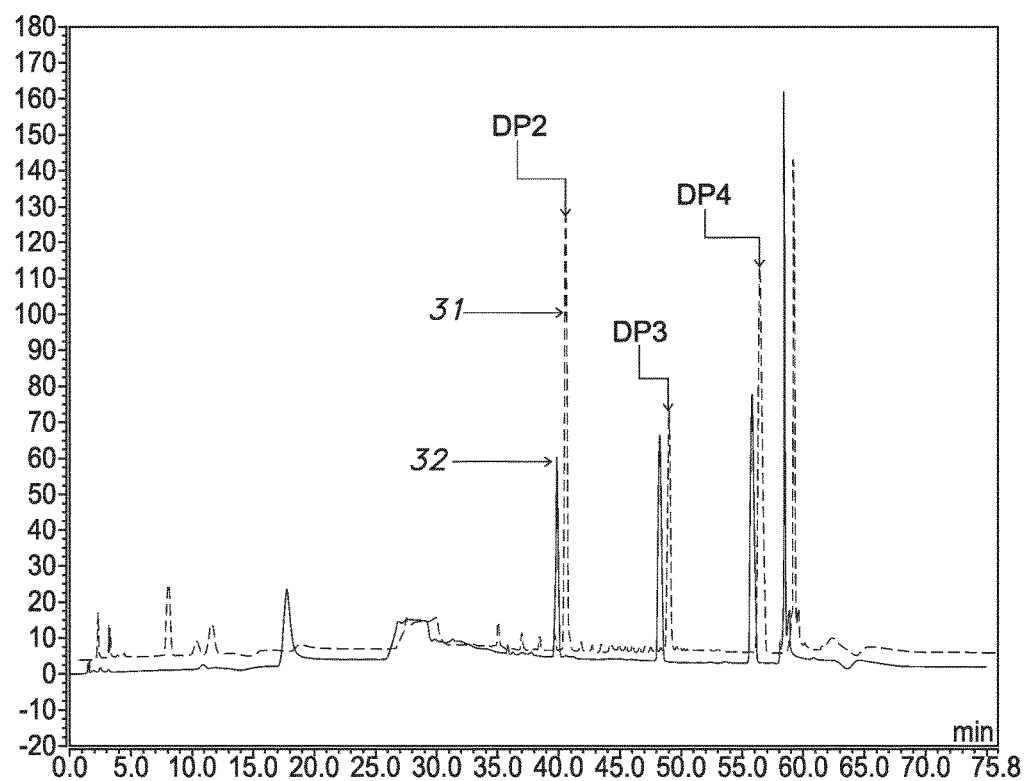
FIG. 4 shows the presence of oligomers after digestion of pectin with polygalacturonase from *Aspergilius aculetus* after high performance anion exchange chromatography (HPAEC) for commercial pectin from citrus peel and pectin obtain with the herein described process.

Also pectin extracted from coffee pulp with the present process, presents same digestion profile as the commercial pectin extracted from citrus peel when treated with endo-polygalacturonase (PG) as can be seen in the high performance anion exchange chromatogram (HPAEC) FIG. 4, while pectin from sugar beet is poorly digested by PG because the branched structure. Other difference is the degree of acetylation and methylation that can be tuned with the present process. However, the raw pectin from coffee pulp presents a unique high degree of acetylation and methylation, this leads to the possibility to produce all range of pectins with different degrees of methylation from 10% DM till as high as 80% DM this is unique for a commercial pectin as well.

Example 3

Experiment Data:

The following experiments were performed with freeze dried samples of coffee pulp (exocarp and mesocarp). The experimental design was as follows: (1) Preparation of freeze dried coffee pulp (FD-coffee pectin): 100 g of FD-coffee (i.e. freeze-dried coffee pulp) pectin was milled in a Retsch ball mill to a particle size that passes through a 6 mm mesh. (2) FD-coffee pectin was homogenized in demineralized water in one liter of water; the pH was adjusted to low pH using Hydrochloric acid (HCl) 37%. The acid was added drop wise. (3) The suspension was placed in a water bath at the correct temperature with continuous shaking for the exact period of time. (4) The suspension was then filtered hot through cheese cloth; the cloth was squeezed by hand to remove most of the liquid from the solid mass. (5) The solid mass was then homogenized with 0.5 l of water and the pH adjusted with NaOH 4M the alkali was added drop wise. (6) The suspension was placed in a refrigerated ice bath with continuous shaking for the exact period of time. (7) The suspension was then filtered in hot through cheese cloth; the cloth was squeezed by hand to remove most of the liquid from the solid mass. (8) Solutions are mixed together, 15 ml of Hydrogen Peroxide (H2O2) was added and the solution is neutralized with NaOH or HCl. (9) 1.5 ml of horse radish peroxidase is added to the solution, and placed in a water bath at 40° C. for 12 hours with continuous shaking. (10) 6 l of cold ethanol 90% is added to the solution and left for 3 h at 4° C. The formed suspension is then filtered through a Whatman 3 cellulose filter paper with the help of vacuum. The retentate is washed with acetone several times to remove impurities. (11) The retentate is dried in a convection oven for 12 hour at 50° C. and maximum air convection. (12) The dried coffee pulp pectin (coffee pectin) is weighed for yield and then milled for composition analysis.

TABLE 4

Results:

| | pH 1 | Temp 1 | Time 1 | pH 2 | Temp 2 | Time 2 | Yield |
|---|---|---|---|---|---|---|---|
| coffee pectin001 | 1.5 | 90° C. | 30 m | 8 | 4° C. | 30 m | 25% |
| coffee pectin002 | 2 | 90° C. | 30 m | 8 | 4° C. | 30 m | 23% |
| coffee pectin003 | 1.5 | 80° C. | 120 m | 8 | 25° C. | 120 m | 20% |
| coffee pectin004 | 2 | 80° C. | 120 m | 10 | 25° C. | 120 m | 30% |
| coffee pectin005 | 2 | 90° C. | 30 m | 13 | 25° C. | 30 m | 5% |
| coffee pectin006 | 2 | 90° C. | 30 m | 10 | 25° C. | 30 m | 33% |

Although yields of extractions were low in comparison to the amounts of pectin reported in the literature, the produced pectin showed surprisingly high amount of methyl and acetyl groups with DM of 80% and DA 100% while normal pectins after extraction do not present DM higher than 75% or DA higher than 50%. Even though alkali hydrolysis is applied in the extraction. Furthermore, the extracts from coffee pectin show gelling behaviour at high pH, this could be the reason why coffee pectin005 shows so low yield due to the fact that in the second extraction, the gel is retained with the cellulose fraction. At this pH substantially all pectin may be hydrolyzed into its monomers which will then get into solution (when the precipitation occurs).

The laboratory size extraction of pectin from coffee pulp was initially performed with freeze dried material. Since coffee pulp is produced in greater amounts that what can be freeze dried in an economical feasible way, a method for avoiding coffee pulp oxidation and fermentation was developed. In a field experiment we used fresh coffee cherries, the fresh pulp was pressed to remove excess of water and the procedure followed was as substantially described above. In this example, preserved pulp was used instead of freeze-dried pulp. For the preservation test we started with sodium bi-sulphite (NaHSO$_3$) which is a common anti browning agent in the food industry and compared also low pH and heat treatment to inactivate the endogenous PPO (polyphenol oxidase) that causes oxidation in coffee pulp. The treatments were done in vitro using cathecol as substrate which is a common polyphenol present in coffee as well as in other plant materials, laccase was used as positive control and a fresh coffee extract was use to oxidise the polyphenols and record the change of absorbance.

After obtaining a satisfactory method for the preservation of the pulp, we proceeded to try the method at large scale (50 kg) of pulp collected from the wet mills. This demonstrate the applicability of the preservation method at large scales, which is needed to be able to collect and preserve the pulp needed to make the process feasible. For the large scale extraction of coffee pulp we used wet preserved pulp (10 kg)

and scale it up trying to follow as much as possible the laboratory process, we obtained low yields from this extraction.

Coffee is one of the most important agricultural commodities in the world. Its most common cultivated varieties are *Coffea arabica* sp. and *Coffea robusta* sp. The total amount of green bean coffee produced in 2011 was 7.8 million ton; demand is estimated to grow 10% in the next decade. Mechanization of coffee production has been carried out for the last twenty years to cope with the demand, this has created new challenges in the coffee chain. On one hand, mechanization increases coffee productivity and lowers cost of production; on the other hand mechanized production generates more agricultural waste and reduces labour force in the plantation. Because of mechanization, coffee discarded streams are being concentrated in the washing stations, where the coffee cherries are transformed into green beans. Today the traditional wet method of coffee processing is being replace by the semi wet method or aquapulping. In the semi wet method the pulp is separated from the beans by mechanical means, the mucilage is removed by friction and mixed with the pulp. The discarded streams are mostly composed of the skin, pulp, mucilage and silver skin of coffee cherries. This discarded stream contains high amounts of polyphenols, polysaccharides and sugars, as well as limited quantities of caffeine. The presence of polyphenols and their oxidised forms and caffeine makes the residue unfit for use as animal feed or as composting material. Thus, these side streams pose a major environmental problem in the coffee producing regions.

Coffee pulp represents about 40% of the total fresh weight of the coffee cherry. Traditionally, coffee pulp was used in small amounts as fertilizer and vermin-composting. However, these applications are not technically efficient for the high scale production of coffee. The pulp biomass is rich in polyphenols, caffeine and complex polysaccharides such as pectin. These substances can be extracted from the pulp, by separating and refining the products following the biorefinery approach. By separating the coffee pulp biomass the pollution loads could be reduced and the refined material could be transformed into valuable biobased compounds, these can be used in the food and pharmaceutical industries.

Freeze-dried material showed stability in terms of oxidation and fermentation in comparison to fresh pulp. However, freeze-drying is an expensive process, and is industrially of less interest for preservation of the increasing volumes of discarded biomass, on the coffee plantations.

Although pectin occurs commonly in most of the plant tissues as a cementing substance in the middle lamella and as a thickening on the cell wall, the number of sources that may be used for the commercial manufacture of pectin is very limited. Because the ability of pectins to form gel depends on the molecular size and degree of degree of esterification (DE), the pectins from different sources does not have the same gelling ability due to variations in these parameters. Therefore, detection of large quantity of pectin in fruit alone is not itself enough to qualify that fruit as a source of commercial pectin. At present citrus peels are the main sources of commercially acceptable pectins.

Commercial pectins are characterised by a high content of galacturonic acid, and this has become part of the legal definition for pectin used as food additives or for pharmaceutical purposes. Typical requirements are of a minimum of 65% of galacturonic acid on the ash and moisture-free substances. Pectin normally comes from a range of botanically different tissues, which perhaps contain somewhat different pectin structures. The traditional sources of pectin are apple pomace and citrus peels, both coming from the left overs of the juice industry. Among the novel sources of pectin are sugar beets and sunflower heads, but these are not, at the moment commercially significant. Extraction of pectins, as showed herein, may be by aqueous acid or alkaline, especially with at least an acid extraction. The basic extraction process yields a pectin of low degree of esterification (low DE pectin) as a result of saponification of the ester groups, whereas the acid extraction process generally yields a pectin of high degree of esterification (high DE pectin), approximately equal to the naturally occurring DE. High DE pectin has a degree of esterification of 50% or greater. Low DE and high DE pectin generally have different uses in foodstuffs, because they gel by different mechanisms. Both are sold commercially.

In the acid extraction process, plant material is treated with acid at temperatures especially between 70 and 90° C. for a time sufficient to remove desired amounts and quality of pectin from the cellulose plant material. Extract juice from the extraction step is separated from the reaction mixture by filtration. Rotary drum vacuum filtration is common in the industry because the cake is very mushy and difficult to handle. The pressed cake can be put through a re-extraction step to extract more pectin before being filtered and dispose of. Pectin is precipitated from extracted juice usually by alcohol precipitation (methyl, ethyl or isopropyl can be used). Salting out with aluminium chloride was used in the past but new regulations do not allow such salt for pectins used in the food or pharmaceutical industries (CODEX *alimentarius*). The precipitated pectin is separated from the precipitating solution by screen filtration or other means; it is then washed, dried and milled to the desired particle size. During processing the pectin may undergo an ion exchange step to put it in the sodium form for ease of use in foodstuffs applications.

Other methods to extract pectin besides acid or alkali extraction have been used with the aim of reducing cost of operation and increase yields of extraction without loosing functionality of the pectin. High-pressure systems could improve pectin yield without polymer chain degradation of pectin, use of enzymes to degrade the cell wall, use of organic acids or new filtration technologies such as cross flow filtration are promising methods to extract pectins in a more sustainable way.

Pectin differentiates not only from their natural source and type of extraction process, different modifications of the pectin molecular structure are possible yielding specific pectins with enhance or unique properties that can be applied in the food, beverage and pharmaceutical industries. Pectins can be chemically de-esterified using acid, alkali or ammonia. Alternative to chemical methods de-esterification can be done by enzymatic treatments. Other enzymatic modifications are possible depending on the structure of the pectin molecule. It has been found that in sugar beet pectin the feruloyl groups esterified some neutral sugars in the side-chains of the so called "hairy regions". It is possible to take advantage of these feruloyl groups in pectin (beet). It is also possible to cross-link the extracted feruloylated pectins by carrying out coupling reactions. Such reactions can be achieved enzymatically by the use of e.g. a polyphenol oxidase, namely a Laccase. This oxidative cross linking of the pectins can add gelling properties to pectins which do not have such capacity. Because the gel is based on chemical bonds, it is also possible to recover the cross linked pectins, after drying. These modified pectins have remarkable water absorption capacities. Coffee pulp is rich in polysaccharides and may be a potential source of pectin. New methods for pectin modification could unlock the potential of coffee pulp, as source of commercial pectin. Taking into account that coffee pulp is a polluting waste with a year output of 20 million metric tons (estimations calculated from ICO), the impacts of this technology could influence the pectin markets. To be able to extract pectins from coffee side streams, methods for preserving the pulp need to be found and tested in the conditions of the coffee plantations. As oxidation is the main post harvest process that transforms this available biomass in an environmental problem in coffee regions. Oxidation of the coffee pulp is mainly due to the enzymatic catalysed reactions of polyphenols with endogenous peroxidases. Information on polyphenols from coffee pulp and polyphenols peroxidase (PPO) activity in the coffee fruit is scarce, and there is no information on how to preserve coffee pulp from oxidation. One of the reasons of this is that, coffee pulp is just a waste stream of the coffee chain and no industrial alternatives are in place for its valorisation. The major problem for coffee pulp usage is the rapid oxidation that takes place after the milling operation. Although is common knowledge that oxidation happens in the coffee pulp, its mechanism has not been understood yet. Part of the aim of this research is to come up with a way to preserve the coffee pulp in such a way that it could be used in a biorefinery scheme.

Figure 5A:
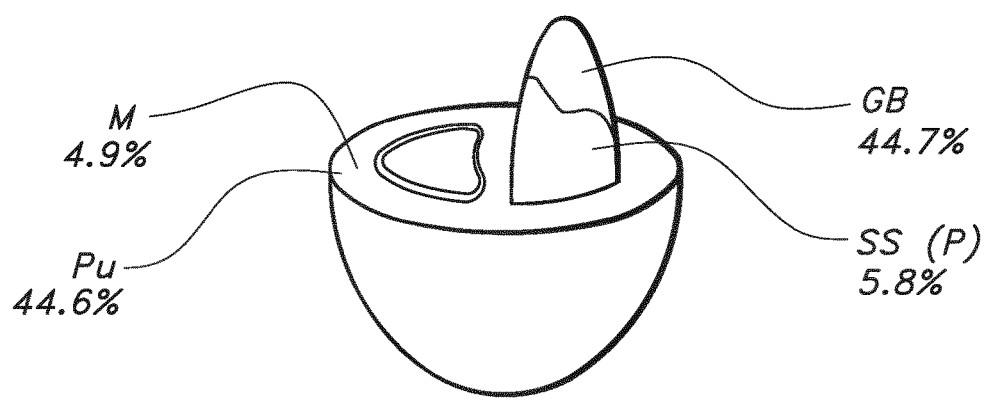
FIG. 5a schematically shows a coffee bean.

The laboratory scale extraction of pectin was done in a field experiment. However, the raw material in this case is fresh coffee cherries. After testing the extraction from fresh material, we proceed to test chemical and physical treatments to stop oxidation of the biomass. Once we obtained a satisfactory preservation process, we used the procedure to preserve a larger volume of fresh coffee pulp. With the preserved biomass, we attempted the scaling up the extraction of pectin. We did composition analysis to the different fractions after extraction. A very schematic drawing of a coffe bean is indicated in FIG. 5a, with characteristic contents in weight percentages, with M indicating mucilage (4.9 wt. %), GB indicating the green bean (44.7 wt. %), Pu indicating pulp (44.6 wt. %), and SS (p) indicating the silver skin (parchment) (5.8 wt. %). These weight percentages are characteristic values that may differ from bean to bean and from type of coffee bean to type of coffee bean.

Methods and Materials

Laboratory Scale Extraction:

We extracted pectin from coffee pulp following the developed procedure in the laboratories with some modifications. Briefly, 10 g of fresh pulp was collected and 50 ml of a Nitric acid solution 1% is added and mixed. We verified the pH to be between 2.0 and 2.5. The pulp is extracted for 3 h at 90° C. with constant stirring. After extraction, the suspension is cool down to room temperature and filtered through cheesecloth. The pressed cake is then mixed with another 50 ml of Sodium hydroxide 0.1% and the pH adjusted to 9.0 with concentrated alkali. The suspension is then stirred constantly for an hour at 10° C. We adjusted the pH again to 7 and filtered through cheesecloth, the solutions are then pooled together. The pH of the solution is adjusted (here to pH=3.5) by adding few drops of concentrated NaOH or Nitric acid solution drop wise. To clarify the solution, we centrifuged the pooled liquid at 2500 rpm for 15 min. Ethanol 96% is added to the liquid in a ratio of three volumes of alcohol per one volume of pectin extract. We carefully mix the solution and left it to precipitate for 12 h at room temperature. We washed the precipitated once with 100 ml of 96% ethanol and dried under current of air for 12 hours. The dry pectin is dissolved in 100 ml of phosphate buffer pH 6.0, the pH is verified and 0.1 ml of laccase solution (18 mg protein per ml) is added. We let the solution react with continuous stirring for 12 h. The solution is then filtered through a Whatman No 2 paper. The clear solution is precipitated again with 0.31 of 96% ethanol and dried under a current of air. 96% ethanol was analytical grade. Laccase was supplied as a freeze-dried powder. We dispersed the Laccase in 0.01M phosphate buffer pH 6.0 and stored at 4° C. until use. The degree of esterification was measured using Megazyme kit for pectin identification. Briefly, coffee pulp, sugar beet, low methyl esterified citrus, high methyl esterified citrus pectins and iota carrageenan are dissolved in water and the pH is adjusted to 12 in order to catalyse demethylation with production of polygalacturonic acid regions in the polymer. The pectate is incubated with pectate lyase which cleaves the polygalacturonic acid, releasing unsaturated oligosaccharides which absorbs strongly at 235 nm.

Preservation Tests:

50 Kg of coffee cherries were collected in the region of Cundinamarca Colombia in the month of May 2013. Hand-picked ripe coffee cherries were transported to a laboratory facility. Upon arrival, the cherries were frozen immediately at −20° C. to avoid oxidation or fermentation. The material was used in the following two weeks.

Laccase was kindly supplied in freeze-dried form. 1 g of powder had 18% protein. We dissolved the enzyme in 10 ml phosphate buffer solution at pH 6.0 and kept frozen in several vials. Each vial was 1 ml (18 mg of protein per ml) and when thawed was immediately used to avoid freeze thawing cycles.

Cathecol was purchased from Panreac, sodium bisulphite, citric and nitric acid where analytical grade. Polyvinyl polyridone PVPP was purchased from a local provider and was food grade quality. AMICON Spin tube membranes MWCO 10.000 were acquired from Millipore corp. We carried out all spectrophotometric measurement with a Pharo 100 spectrophotometer (Merck Millipore).

The method for measurement of PPO activity in coffee pulp is in brief as follows: 250 g of frozen coffee cherries were macerated and the bean with mucilage and silver skin were separated from the pulp. The total pulp obtained was 112.70 g in fresh basis (f.b.). This pulp was then blended together using a hand mixer with 0.41 of a 50 mM phosphate buffer at pH 6.0. We left the blended mix to settle for 10 min and filtered. We collected the supernatant, an aliquot of 10 ml of the supernatant was taken, aprox. 0.1 g of commercial insoluble PVP was added. The mix was shaken for about a minute and then centrifuged for 15 min at 10.000 RPM the mix was kept at 4° C. before analysis.

We took 3 ml of the supernatant, add it to an Amicon MCWC of 10.000 Da membrane and centrifuged for 30 min at 10.000 RPM. This procedure was repeated in the same membrane 3 times. With 1 ml of phosphate buffer 50 mM pH 6.0, the remnant on the amicon membrane was wash three times, solubilised and reserved in an amber vial at 4° C. This is the enzyme extract of coffee pulp (EX). A solution of 60 mM of Cathecol was prepared in a 50 mM phosphate buffer pH 6.0 and used as substrate. For measurement, we used a 1 cm light path length cuvette, 50 ul of substrate and 50 ul of EX added to 2.9 ml of distilled water and the absorbance followed in at 420 nm after 1 h, 2 h, 12 h and 24 h.

Large Scale Preservation and Extraction

We collected coffee pulp in two batches from two different types of beneficio (Post-harvesting process). The first 126 kg batch was collected from a traditional wet mill operation. In the traditional wet processing method, cherries are transported with water through the pulping machine in a ratio of 4 litres of water per kilogram of cherries. To remove excess of water the pulp was taken from the output pipe of the pulping machine with a strainer. The pulp then was placed in hermetic barrels (3 barrels of 60 L each) which were filled 70% of the total volume with pulp. The barrels then were filled to the top with a solution of 1% of sodium bisulphite solution commercial grade, and sealed air tight for transportation. The ratio of solution to pulp was about 1 litre of solution per kilogram of fresh pulp.

The second batch of 96 Kg was collected from a semi wet method mill operation (Belcosub or aquapulping). In this method, a mechanical screw transports the cherries through the pulping machine without water. Then the beans with the mucilage go through a scrubbing process, where the mucilage is removed. The pulp and mucilage are mixed together, and discarded or composted. The pulp from this type of beneficio was collected immediately after the milling operation by placing the barrels in the pulp outlet. Since there was less water in the pulp than for the traditional method, the barrels were filled just 60% of the volume, and then filled to the top with a sodium bisulphite solution at 1%. The ratio of solution to pulp was higher due to the packing of the pulp in the containers. The ratio was 0.81 of solution per kilogram of pulp. The coffee pulp collected and preserved in a sodium bisulphite solution was periodically checked for oxidation by change in absorbance of the solution. For that, 100 ml of the solution in which the coffee pulp was suspended was taken every 24 h, centrifuged and the absorbance of the solution measured at 420 nm.

For the extraction of pectin from the preserved fresh pulp, we took 10 kg of biomass taking care to remove excess water; we mixed the pulp with 40 L of a 1% solution of nitric acid and blended with an industrial hand mixer at maximum speed (18.000 RPM) for about 10 minutes. Once the mixture was homogenized, we heated it with constant stirring to 92° C. for 3 h. After cooling down, we separated the solids with a strainer, and mixed with diatomaceous earths (DIE) as filter aid in a proportion of 1 kg of DIE per 10 L of liquid. We filtered the suspension using a frame and plate filter of 2.8 m² of surface. The membranes were of 100 μm pore size constructed with nylon. The liquid is reserved and the cake is pressed to remove excess of water. We mixed the residual cake with 40 L of NaOH 0.5% and stirred constantly for one hour. The suspension was then neutralised (pH 7.0), the solids pressed and the liquid filtered using the same press filter system and DIE. We mixed both alkali and acid extracts, adjusted the pH to 5.0, homogenized and filter it one more time to obtain a clear solution.

Figure 5B:
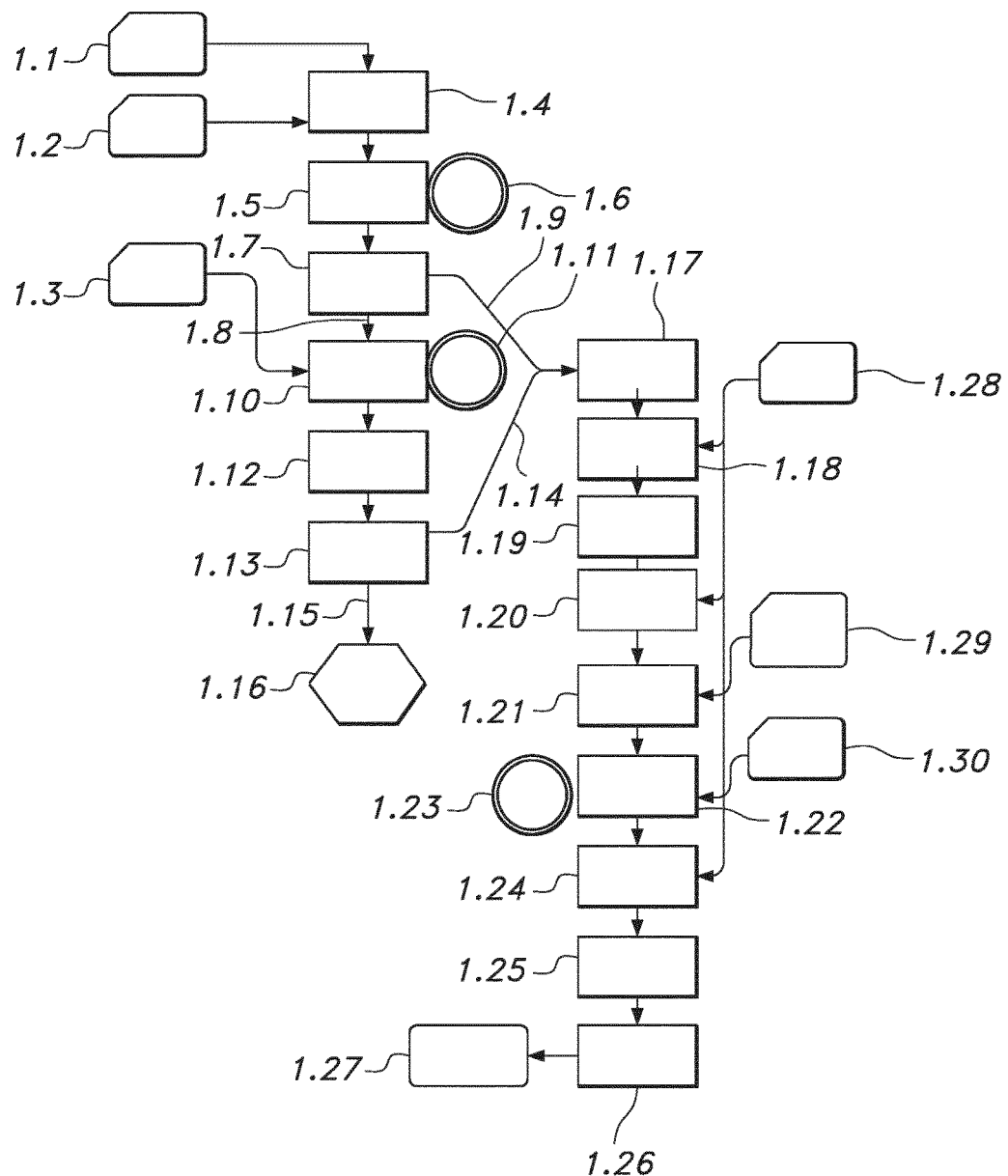
FIG. 5b shows a (Laboratory) scale process for fresh material.

The clarified liquid is the raw pectin liquor. This liquid was mixed with one volume of ethanol 96% (Industrial grade) per volume of liquor. The pectin was left to precipitate for 12 h. The solution with the gel was filtered using cheesecloth; the filtration bag was hoist to allow dripping of the residual ethanol solution for 24 h. The remaining gel was dried at room temperature under a current of air (electric fan). The dried pectin was dissolved in 5 L of a phosphate buffer solution 0.1M and pH 6.0, then 5 ml of laccase (18 mg/ml) were added and the enzyme was left to incubate for 12 h. We mixed the modified pectin solution with one volume of ethanol 96% and let the modified pectin to precipitate for 24 h. The suspension of pectin with ethanol is filtered through cheesecloth, pressed and dried under a flow of air at room temperature. FIG. 5b shows the flow chart for a scale extraction of 10 kg, with the following references.

TABLE 5 references of FIG. 5b

| Ref. | Meaning |
|------|---------|
| 1.1 | Preserved Pulp 10 g |
| 1.2 | Nitric acid 1% 50 ml |
| 1.3 | NaOH 0.1% 50 ml |
| 1.4 | Homogenization |
| 1.5 | Acid extraction |
| 1.6 | T = 90° C. t = 3 h pH = 2.0 |
| 1.7 | Filtration |
| 1.8 | Cake |
| 1.9 | Filtrate |
| 1.10 | Alkali extraction |
| 1.11 | T = 10° C. t = 1 h pH = 9.0 |
| 1.12 | pH Adjust |
| 1.13 | Filtration |
| 1.14 | Filtrate |
| 1.15 | Cake |
| 1.16 | Residue |
| 1.17. | Homogenization pH adjust |
| 1.18 | Alcohol precipitation |
| 1.19 | Filtration |
| 1.20 | Washing |
| 1.21 | Resuspension |
| 1.22 | Enzymatic reaction |
| 1.23 | T = 20° C. t = 12 h pH = 6.0 |
| 1.24 | Alcohol precipitation |
| 1.25 | Filtration |
| 1.26 | Drying |
| 1.27 | Modified Pectin |
| 1.28 | ETOH 96% 400 ml |
| 1.29 | Amonium Butter pH 6.0 50 ml |
| 1.30 | Laccase 18 mg/ml 0.1 ml |

Results and Discussion

Laboratory Scale Extraction

For the laboratory size extraction, we used fresh coffee cherries, the extraction procedure is depicted in FIG. 5b. The procedure differs from the one developed before in the (optional) press of the fresh pulp while before we used freeze dried pulp. Coffee cherries have variations in their composition not only between species (*Arabica* or *Robusta*) but also between varieties. As most of the small coffee farms have a mixed of varieties, the composition can also change from farm to farm or harvest to harvest. The average composition of a coffee cherry is depicted in 5a. To start the extraction procedure the first step is to separate the pulp from the bean when we use the whole coffee cherry. In the coffee plantations, this step is done mechanically by pressing the cherries against a screen that remove pulp. Because in the traditional operations the cherries are transported with water, it is possible that the pulp soaks water during the process. In the laboratory, the water content of the fresh coffee pulp was 73% of the total mass. But for preserved coffee pulp in the sulphite solution, the water content was 80%. To have an average solid percentage of biomass for the extraction we first pressed the pulp. The juice that came out was mixed with ethanol and some small precipitate formed. After drying the precipitation we obtained 10 mg of dried mass, most probable the soluble free pectin. The juice as it is have low pectin content since the pectin is tightly bound to the cell wall, one of the reasons to avoid milling of the pulp before preservation is to reduce the loss of pectin in the pressing. From 100 g of pulp, 38.6 g of juice were squeezed out. The pressed pulp had a water content of 50%. When compared with the pulp from the semi-wet method the juice squeezed from the same amount of pulp was only 20 g and the water content was 41%. Most probable the mucilage adds to the dry mass of the pulp. After obtaining the pulp we did a composition analysis. Table 6 displays the results of the coffee pulp in dry basis.

TABLE 6

Coffee pulp composition in dry basis

| Material | Wt. % |
| --- | --- |
| Protein (N * 6.25) | 8.2% |
| Lipids | 1.3% |
| Fibre, crude | 30.5% |
| Ash | 5.7% |
| Carbohydrates | 54.1% |

After pressing, we took 10 g of pulp to proceed with the pectin extraction as described in the flow chart in FIG. 5b. When we mixed the pulp with the acid solution the first change is the colour of the pulp. From the more brown yellowish colour due to the sulphite preservation, becomes a bright red colour. This is most probable due to the change in charge of the polyphenols and it will be discussed in the section of preservation. During acid extraction is evident how the pulp soaks water, if temperature is not controlled to avoid evaporation, then the suspension becomes so thick that can burn. After the acid extraction the filtration is one of the most critical steps in the process. The best method until now, for filtration is through cheesecloth. Applying pressure is the best way to remove as much as possible the liquid that has been soaked by the biomass. Usually after pressing, the biomass has between 10% and 15% of water. At this point the composition of the residue was analysed, in Table 7 the results for the biomass in dry mass after acid hydrolysis.

TABLE 7

Residue of coffee pulp after acid hydrolysis and filtration

| Material | Wt. % |
| --- | --- |
| Protein (N * 6.25) | 16.7% |
| Lipids | 2.1% |
| Fibre, crude | 27.2% |
| Soluble fibre | 12.1% |
| Ash | 10.5% |
| Carbohydrates | 40.2% |

When suspended again in the alkali solution a rapid change of colour is visible. The light brown to the very green dark of the pulp in this step depends much in the pH of the system. At pH under 8.0, the pulp is light brown and the viscosity of the biomass is appreciable. When the pH is set to 9.0, the whole mix becomes dark brown and the viscosity is lower (observation). One of the reasons to use an alkali and acid extraction is to achieve higher yields for pectin extraction. Table 7 shows that the acid residue still has a high content of sugars (carbohydrates). This makes evident that harsher conditions are needed to extract pectin. In other sources of pectin such as sugar beet pulp, many authors have used alkaline treatments, the procedures comprises extraction and de-esterification in alkaline medium, followed by acid washing to remove ashes and drying. Turquois et al demonstrated that under alkaline conditions, sugar beet pulp and potato pulp yields products containing a high content of pectic substances estimated on the basis of galacturonic acid contents and producing firm gels with calcium ions. As acid and alkali treatments give different properties and with the aim to maximize yields both extractions are done in sequence. In Table 8 the composition of the biomass, after alkaline treatment of the acid residue. By comparing both table two and three, it is clear that the carbohydrates are lower after the alkali treatment. Moreover, the fibre and carbohydrate contents are quiet close, this means that most of the polysaccharides in the alkaline residue is composed by cellulose which is the main component of the crude fibre. In both tables the content of protein is quiet high, residual nitrates from the acid may overestimate the protein content.

TABLE 8

Composition in dry basis of the coffee pulp after sequential extractions with acid and alkali (pH 9.0)

| Material | Wt. % |
| --- | --- |
| Protein (N * 6.25) | 14.3% |
| Lipids | 2.7% |
| Fibre, crude | 35.5% |
| Ash | 8.8% |
| Carbohydrates | 33.0% |

After alkali extraction the filtrate is neutralized and both liquids pooled, again pH have an important effect in the behaviour of the pectin in solution. When pH is raised to 9.0 and then neutralized and combine with the acid extract solution there is the formation of a instant gel. Whereas if pH is raised to 8.0, neutralized and pooled with the acid extract solution there is no gel formation. This may be a result of the de-esterification of the pectin molecule at high pH. This give a major contradiction, if coffee pectin extracted by alkali can form such gels when acidified, then the molecular size is big enough to form networks in water systems. This as a corollary tells us that the pectin extracted with acid are different from the alkali extracted since acid pectins do not show calcium sensitivity or gelling behaviour before enzymatic modification.

When pH is kept at 8.0 during alkali extraction, neutralized and pooled with the acid extract the resulting liquid is homogeneous after mixing. To remove the polyphenols from the pectin is necessary to precipitate with Ethanol the pectin and then washed several times. After washing with solvent, the precipitate is dissolved in Ammonium phosphate buffer pH6.0 0.1M. Laccase is added to the dissolved pectin in a ratio of 0.01:1 grams. After reaction for 24 hours with the enzyme, the solution shows a colour shift and higher viscosity (observation) compared with the original solution.

Coffee pulp has an important content of polyphenols. We measured the content of polyphenols by the Folin Ciocalteau assay with tannic acid as standard and the flavonols by the Vanilin method. The results for whole coffee pulp is in Table 9.

TABLE 9

Content of phenol compounds and flavonols in coffee pulp

| Material | Wt. % |
| --- | --- |
| Phenols | 1.8% |
| Flavonoids | 1.3% |

Coffee pectin show abundant hairy regions and feruloyl groups. It is possible that the reactions happening during the enzymatic modification is in effect an oxidative cross linking of the coffee pectin. The colour of the solution changes also by the modification from light to dark. The gel thus obtained needed several washing to remove the formed colour during the incubation.

After modification, coffee pectin is precipitated with ethanol and dried under a flow of air at room temperature. The yield from 10 g of coffee pulp is 25 mg of unrefined pectin. Table 10 shows the composition of coffee pectin. Table 11 presents the mass balance of the laboratory scale extraction from dry freeze coffee pulp and fresh pulp in dry basis.

TABLE 10

Composition of coffee pectin after modification

| Material | Wt. % |
| --- | --- |
| Protein | 15.2% |
| Soluble fibre | 47.0% |
| Insoluble fibre | 0.4% |
| Ash | 10% |
| Flavonols | 2% |
| Phenols | 3% |

TABLE 11

Mass balance for each extracted fraction from freeze-dried and fresh coffee pulp

| Fraction | Freeze-dried pulp % | Fresh pulp % |
| --- | --- | --- |
| Dry mass | 91 | 25 |
| Carbohydrates | 60 | 54 |
| Acid extract | 21 | 14 |
| Alkali Extract | 12 | 7 |
| Residue | 13 | 20 |
| Soluble sugars* | 14 | 13 |

*Soluble sugars where calculated as the difference of the yields with the carbohydrate content To clean the pectin we had to wash several times with alcohol and methanol, it was more difficult to clean the laccase-incubated pectin than the extracted non modified pectin. After several washes with ethanol and methanol (pure) we obtained a gel with a light pink colour. We collected the gel and dried at room temperature (20° C.) under flowing air for 24 h. After the gel was completely dried, we grinded it in a ceramic mortar by hand. This we denominated modified coffee pectin (MCP). The extract without modification was also washed with solvent and dried under the same conditions, this pectin was denominated coffee pectin (CP).

With the modified coffee pectin (MCP) we measured the content of unsaturated uronic acid residues in the pectic polysaccharides. The analysis measured the activity of pectin lyase which cleaves the 1-4α D galacturonic acid bonds. When these are unsaturated (no presence of methyl or acetyl groups) and by comparing with known pectin samples the content of unsaturated oligosaccharides can be extrapolated. The results are summarized in Table 12 below:

TABLE 12

Analysis of the concentration of unsaturated pectin according to JECFA (Joint FAO/WHO Expert Committee on Food Additives)

| Polysaccharide | Unsaturated product × $10^{-4}$ M |
| --- | --- |
| HECP (high ester citrus pectin) | 3.10 |
| SBP (sugar beet pectin) | 2.03 |
| MCP (modified coffee pectin) | 0.285 |
| CP (coffe pectin) | 0.476 |
| Carrageenan | 0.004 |

Pectin molecular weight is calculated as polygalacturonic acid with extinsion coefficient of $4600 M^{-1} cm^{-1}$ These results show the difference between sugar beet pectin (SBP), MCP and high ester citrus pectin (HECP). The lower the value in the table, the less free places the polysaccharide has to form hydrogen bonding or to interact with ions. This can explain why CP (coffee pectin) and MCP (modified coffee pectin) do not gel and therefore it opens the possibility to use enzymes like pectin methyl esterases (PM) or alkali treatments to demethylate the polysaccharide. Other important characteristic of MCP is that its unsaturation is lower than SBP, this of course shows that although both are pectins, the products in itself are molecularly different. Furthermore, it shows that MCP has a more hydrophobic nature than HECP or SBP and if you add the content of protein, its application as food additives could be clearly in emulsification, but also in other completely new applications. Hence, this identification test indicates qualitatively the difference sources or type of pectin. It shows that coffee pectin is indeed different from Citrus pectin and SBP. This is unique for the hydrocolloids soluble in water. For the analysis of table 12, the Megazyme kit for pectin identification was used, according to the Assay procedure K-PECID 11/11 (Megazime International Ireland 2011).

Preservation

To understand the oxidation development of phenolic compounds present in coffee pulp, it was necessary to extract the enzyme(s) that catalyse the reaction while avoiding the oxidation of such compounds. In previous literature authors have extracted and characterized the enzymes responsible for oxidation in the coffee leaves and endosperm (beans). They found that the enzymes responsible for the oxidation are from the family of polyphenyl peroxidases PPO (E.C. 1.10.3.2). These types of enzymes contains copper in their active sites and are responsible for the hydroxylation of monophenols to o-diphenols and the sub sequential oxidation from o-diphenols to o-diquinones. PPO enzymes are responsible for the enzymatic browning in most fruits and plants. Browning is the results from both enzymatic and non-enzymatic oxidation of phenolic compounds. The initial oxidation products are quinones, which rapidly condense to produce relatively insoluble brown compounds (melanin). The most important factors that determines the rate of enzymatic browning of fruits and vegetables are the concentration of both PPO and phenolic compounds presents, the pH, the temperature and the oxygen availability on the plant tissue PPO enzymes from coffee showed two distinctive bands in a SDS-PAGE, these bands are in 64 and 29 kDa of size. The purified PPO showed higher affinity with chlorogenic acid (Km=0.14 mM) DOPA (Km=1.36 mM), catechol (Km=4.75 mM) and pyrogallic acid (Km=6.16 mM) respectively. As known in the art, the quantity Km indicates the kinetic of conversion in a minute of the enzyme with different substrates. Km is the Michaelis constant. Although it was expected that chlorogenic acid has more affinity to PPO, the oxidation of this compound proceeds faster than other phenols such as cathecol. It was decided to use cathecol to have a better control in oxidation process, also the colour formation of cathecol has been used by other authors due to its increase in absorbance at 420 nm when oxidized. We decided to extract all enzymes complex of the pulp and follow the oxidation of cathecol as substrate using the enzyme extract. When subjected to concentration of the enzymes from the coffee pulp it is important to mentioned that the retentate in the Amicon membrane was a dark brown colour. In the extraction PVPP was used to bound mono and diphenols that could be in solution. After centrifugation, it was visible that many of the colour compounds in the coffee pulp extract are retained, this could mean that polyphenols are bound to bigger molecules like proteins and polysaccharides. The coloured compounds did not elute through the membrane which should let pass molecules smaller than 10 kDa. Because the objective was to test the inhibition of the enzyme(s) by addition of chemicals (sodium bisulphite) or by temperature treatments in processing circumstances, we kept all possible enzyme sizes that can have an effect in the oxidation of polyphenolic compounds. The extract of the enzyme was used as it was extracted from the Amicon membrane, and suspended in 50 mM phosphate buffer at pH 6.

Inhibition In Vitro:

To calculate the oxidation inhibition, the change in absorbance after 24 h of the solution with enzyme and substrate was compared, with the change of absorbance of the samples with sodium bisulphite solution or when temperature was applied. For the inhibition with sodium bisulphite, there was a decrease in the absorbance of the enzyme extract solution without added cathecol. There is a clear interaction of the bisulphite solution with the coloured compounds in the coffee enzyme extract. This also reinforces the idea that polyphenols could be part of bigger molecules that were not eluted through the Amicon membrane. Or the polyphenols themselves are polymers bigger than 10 kDa. Interactions of proteins and polysaccharides with polyphenols such as resorcinol and cathecol have been studied in the past. The interactions of bovine serum albumin (BSA) with cathecol show that complexation is reversible, and is driven by nonspecific surface phenomena. This complexation occurs via both hydrogen bonding of the polyphenol to the exterior ketoimide, and polar groups on the protein and hydrophobic interactions. These mechanisms may be dependant of the protein concentration and the pH of the. Polyphenols concentrations in coffee pulp are high. Protein was also analysed in the fresh coffee pulp and it was found to be 8% (d.b.) (Table 6). If proteins from the same coffee extract go into solution when blending, the polyphenols could bind to the proteins. Because the extraction takes place at a pH where the binding of polyphenols to proteins such as BSA have been found to be favourable, the same binding process could happen with the proteins from the coffee pulp.

The sample subjected to temperature without substrate showed an increase in absorbance, in comparison to the same sample without temperature treatment. This was expected since temperature increases the rate at which oxidation occurs. In the sample with only substrate, there was also an increase in absorbance. The inhibition percentage was corrected for those changes by subtracting the absorbance of the enzyme solution without substrate, which as can be observed in Table 13 has higher absorbance after 12 h of incubation at room temperature (20° C.).

TABLE 13

Light absorbance measured at 420 nm after 12 h for the oxidation of cathecol (substrate)

| Treatment | Substrate blank (AU (absorbance units)) | Enzyme extract blank (AU) | Oxidation reaction (AU) | Oxidation Inhibition % |
|---|---|---|---|---|
| None | 0.072 | 0.158 | 0.385 | 0% |
| Sodium bisulphite | 0.063 | 0.095 | 0.083 | 105% |
| Temperature | 0.137 | 0.171 | 0.184 | 94% |

Figure 5C:
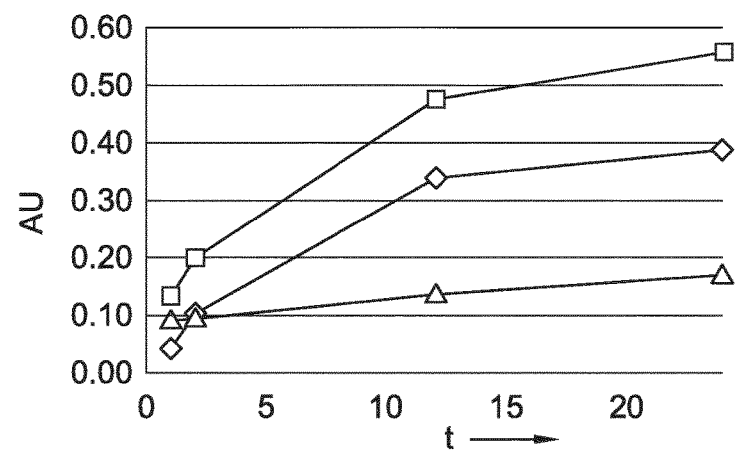
FIG. 5c shows the oxidation of cathecol by PPO from coffee pulp in time (in absorbance units, y-axis, and with time in hours on the x-axis). Data are obtained spectrophotometrically at 420 nm. The sing ◊ indicates the absorbance change of the enzyme extract (indicated with square), minus the absorbance change of the substrate solution (indicated with triangle), without enzyme.

Sulphite compounds can be used to avoid oxidation in foodstuff. As we showed in FIG. 5c, the coffee enzyme extract oxidizes cathecol, but in the presence of sodium sulphite the oxidation is stopped as is showed in Table 13. The enzyme extract is a mix of naturally occurring endogenous enzymes; PPO is present in this extract. The oxidation of cathecol shows that the main reaction contributing to browning of the coffee pulp is the oxidation catalysed by the PPO.

Temperature is another way to stop browning of fruits and vegetables. PPO may be inactivated when subjected to temperatures over 40° C. As the majority of processes for thermal inactivation are intended for fresh fruits and vegetables, it is desirable to expose the product as less as possible to higher temperatures in order to preserve appearance of the product. In the case of coffee pulp, the inhibition of the enzymatic browning is desired for preservation of the biomass so posterior processes can be applied. As appearance or texture of the product is not of importance, coffee pulp can be subjected to higher temperatures and longer times. However, the impact of such treatments on the final quality of pectin has to be assessed. We decided to heat the coffee enzyme extract for 30 min and 90° C. so to mimic a normal blanching step for the pulp, in such way not only PPO but other enzymes as well as fungal activity will be stopped. As can be seen in table 13, temperature also inhibits enzymatic browning, however it also catalyzed oxidation therefore the change in absorbance between the substrate blank, the enzyme blank and the oxidation sample. The higher absorbance compared to the sulphite could be due to the non enzymatic oxidation of the polyphenols present in the coffee extract as well as the oxidation of cathecol by the presence of oxygen. In any case, temperature could be applied in coffee pulp to stop enzymatic browning.

Large-scale Preservation of Coffee Pulp:

As sulphite solution gave positive results for inhibition of oxidation, we use a 1% solution of sodium bisulphite to submerge the pulp collected from the wet mills.

In the first 24 h there was a change in the pulp's colour from a dark brown to more clear yellow. Nevertheless, there was no change in the absorbance at any point at 420 nm. The clear yellow colour of the solution was stable during the rest of the analysis (15 days) after which there was clear evidence of fermentation in the container. It is important also to mention that in the first 3 days of the assay the coffee pulp that was in the surface and not immersed in the Sodium bisulphite solution, changed colour (dark brown pigment), and was attacked by fungi (presumably white rot by microbiological analysis, not shown). However, all the rest of the pulp which was submerged in the solution continued to lose pigmentation (from the red colour of the coffee cherries to yellow colour of the solution) and no attack of fungi was registered. Therefore, to continue the experiments the layer of oxidized pulp was removed and weight was applied to the biomass to keep it submerged in the solution.

The use of the sulphite solution solves a great logistical problem since in this solution the coffee pulp can be preserved for longer times. However, after some time (20 days) The pulped that was preserved in the sulphite solution started to ferment. To keep the integrity of the pectin fermentation has to be stopped; a better preservation form has to be implemented. Drying of the pulp could solve the problem of fermentation and reduce transportation costs. Possible drying technologies that can be applied to coffee pulp based on technical and economic factors may include one or more of: batch drying, sun drying, tunnel driers, belt driers and rotary driers. For batch driers one of the limiting factors is the compressibility of coffee pulp. For the other four technologies the capacities are calculated according to the production of pulp for a medium size wet mill per day. At the peak of the season a medium size wet mill can produce 63.50 metric tons of pulp per day, the authors use the maximum content of water that the pulp have which is 85%. Therefore is necessary to remove 52.16 cubic meters of water in 8 h to obtain coffee pulp with 10% moisture content.

Drying will be a mayor cost for the use of coffee pulp biomass. At the moment coffee pulp is been dried under constant airflow close to a sun dry system, this takes around 8 days with a load of 20 Kg per square meter. We have found that after blanching and pressing the pulp this time is reduced to 2 days at the same conditions.

When the pulp is stored in the sulphite solution the biomass can be transported, when drain and press, The pulp do not show oxidation. After draining, the pulp was placed in trays for sun drying, after one day the pulp showed fungal growth. We checked the pH of the biomass and found it to be 6.0. This pH is optimal for fungi, this is why we decided to adjust the pH of the biomass to 3.5 just before blanching. The result is that the biomass turn colour to bright red, and after several days of drying there is no evidence of fungal growth or oxidation. However when we press the pulp we are losing soluble pectins, taken into account that blanching at low pH could lead to hydrolysis, preserving and drying the pulp could lead to low yields of pectin. The flow chart for the preservation of coffee pulp at large scale is as follows in FIG. 5d with the following references.

Figure 5D:
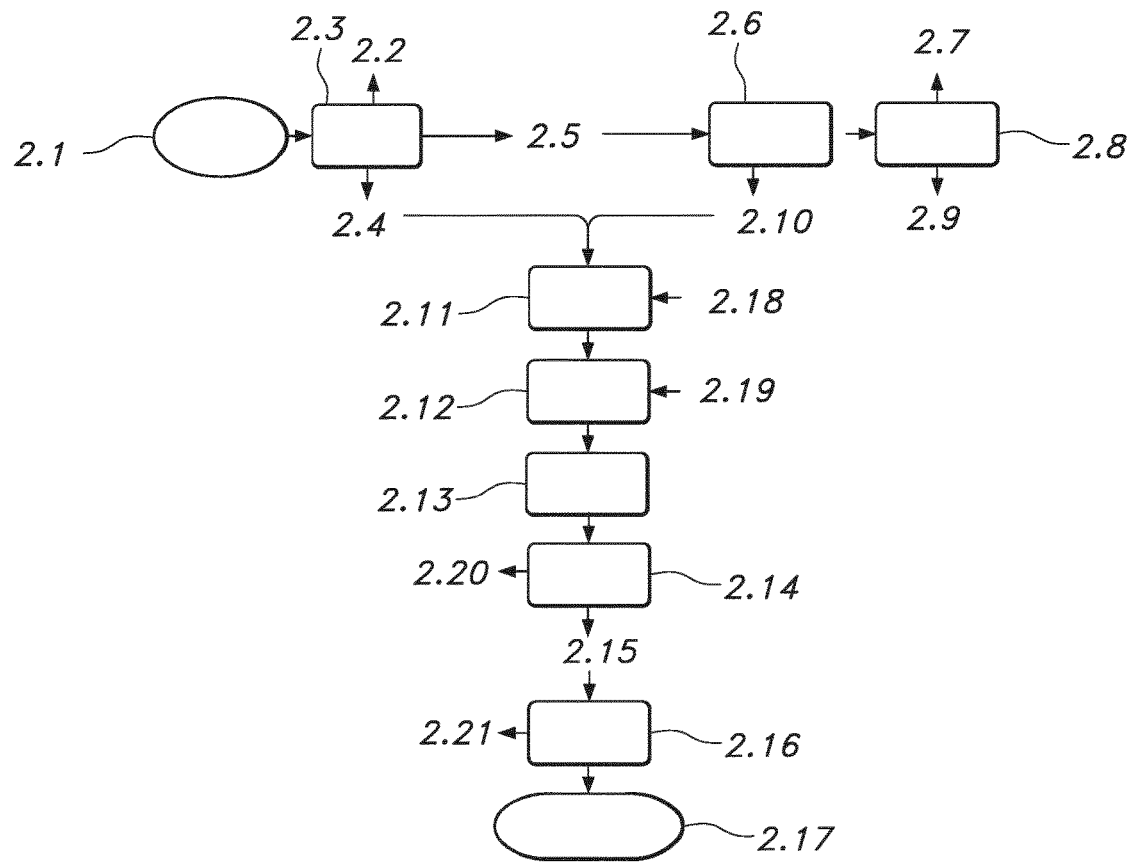
FIG. 5d shows a flow chart for large-scale preservation of dried coffee pulp.

TABLE 14 references of FIG. 5d

| Ref. | Meaning |
| --- | --- |
| 2.1 | Coffee cherry 100 Kg |
| 2.2 | Losses 1.26 Kg |
| 2.3 | Depulping |
| 2.4 | Pulp 44.84 Kg |
| 2.5 | Mucilage + parchment 56.15 Kg |
| 2.6 | Demucilaginator |
| 2.7 | Dry coffee parchment 25.02 Kg |
| 2.8 | Drying |
| 2.9 | Water 22.96 Kg |
| 2.10 | Mucilage 8.17 Kg |
| 2.11 | Sulphite soaking Storage |
| 2.12 | pH Adjust |
| 2.13 | Blanching |
| 2.14 | Press |
| 2.15 | Pressed pulp 27 Kg |
| 2.16 | Drying |
| 2.17. | Dried preserved pulp 10 Kg |
| 2.18 | NaHSO3 1% 44.84 L |
| 2.19 | Nitric Acid 20% 0.22 L |
| 2.20 | Juice 71 L |
| 2.21 | Water 17 Kg |

The preservation procedure allows to keep pulp stable for longer periods, although its stability and the impact on pectin quality have not been assessed. We already extracted pectin from preserved materials with similar results as the freeze dried one. We have not tested the performance of the pectin in any applications yet.

Large Scale Extraction of Pectin from Coffee Pulp

The first problem when scaling the process with wet preserved pulp is the homogenization of the biomass with the acid. Blending the biomass gives a coarse mix, to increase yields is necessary to reduce the particle size of the pulp. We tried to use a rudimentary extruder to achieve the milling of the pulp. The results were not good since the pulp blocks the extruder die very fast. The water holding capacity of the biomass probably causes this problem. So the only way to achieve a good mix was with an immersion blender. However, the milling of the pulp has to be optimized in the future for larger extractions or volumes.

For the first large scale extraction our starting material was the pulp collected from the traditional wet milling process. The pulp was preserved in the sulphite solution (1%), and no oxidation was visible. We took the pulp with a strainer and press out enough of the water in order to maximize the amount of solids. The water leached from the pulp showed turbidity. This could be pectins and other soluble material that are in suspension, because during transport we had some spillage of water it was not possible to do a mas balance on the liquid itself. Though, it was visible that the pulp had soaked in sulphite solution. When the drained pulp was mixed with the acid solution, the colour of the mix turned to red. As discuss before this is probably the effect of pH change of the polyphenols. When heated the sludge separates very fast so constant mixing was needed to keep the biomass in contact with the acid solution.

The solution had a bright strawberry-red colour, but the viscosity was not high. However, the load of suspended solids was. The brix of the solution was 15°. Calculation of the brix by refractometry was not accurate, due to the precipitation of some of the solids over time. It was clear that there were fine particles suspended in the solution, this fouled very fast any cheesecloth or filter paper that we tried. To get a clear solution the particles had to be removed. At laboratory scale, we removed all solids by filtration through a paper filter Whatman #2 (100 um) by vacuum filtration or with a cheesecloth. At large scale the cheesecloth was inefficient and we lost a lot of material.

With the amount of solution to be filtered, an efficient process had to be used to get rid of the particles. We opted for a traditional plate press filter of 20 cm×20 cm and seven frames (0.28 $m^2$ filtration area, Tellarini pompe Italy). Initially we used the same Whatman #2 paper as membranes, which we also used in the laboratory. Unfortunately, the result was very low, since the filter paper got blocked almost immediately (fouling). To make filtration possible we designed synthetic fabric membranes of 100 um particle diameter custom made to the size of the filter press. With the newly made membranes, the filtration improved, but still the operation cycle was too short with less than one litre of solution per cycle. The membrane manufacturers then recommend us to use a filtering aid, in this case diatomaceous earths (DIE) was the best performing material. So we mixed the solution with 1 Kg of (DIE) for every 10l of solution. From less than a litre per cycle, we increased the efficiency to seven litres per cycle. The suspended particles stick to the DIE and form a filtration bed in the membrane. After the cycle, the formed cake can be washed for the recovery of the suspended particles and the DIE. We recovered a portion of the suspended particles and did a composition analysis. The particles are composed by 23% protein and 51% carbohydrates, these particles could be of interest in the future.

After filtration, the brix content of the solution was 10°. Then we added ethanol in a ratio to the solution of 4:1. We measured the percentage of ethanol with an alcoholimeter (percentage in v/v) and found out the solution was over the recommended value. This means we could lower the amount of ethanol for effectively do the precipitation, in the next batches we corrected this value to achieve only 70%, the correct amount of ethanol was 1:1 ratio v/v.

Figure 5E:
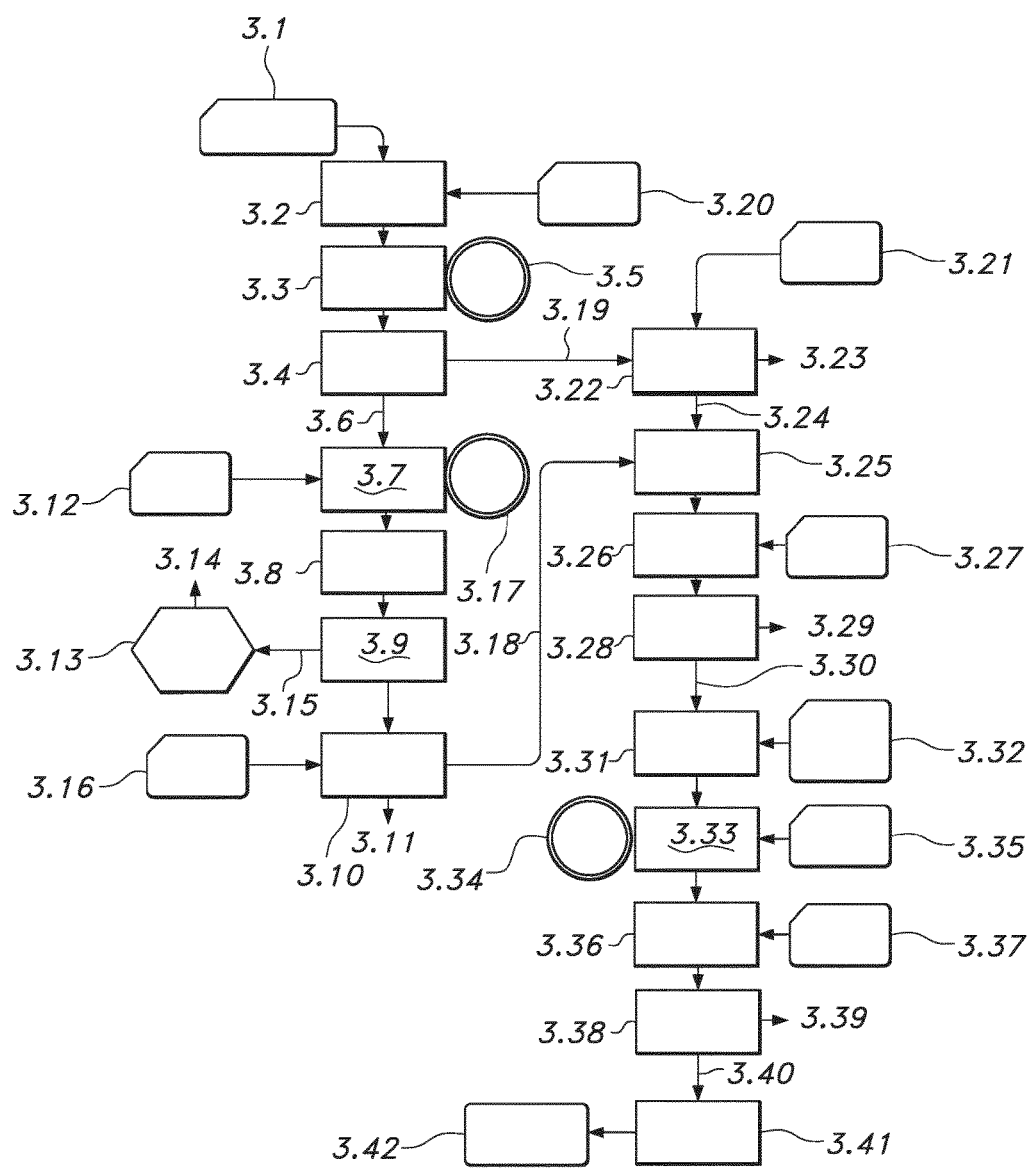
FIG. 5e shows a large scale extraction from preserved wet pulp (with mass balance).

After fixing the ethanol concentration and the filtration problems we proceed to a big scale extraction following the flow chart process in FIG. 5e with the following references:

TABLE 15 references of FIG. 5e

| Ref. | Meaning |
|---|---|
| 3.1 | Preserved pulp wet 10 Kg |
| 3.2 | Homogenization |
| 3.3 | Acid extraction |
| 3.4 | Press |
| 3.5 | T = 92° C. t = 3 h pH = 2.0 |
| 3.6 | Cake 20 Kg |
| 3.7 | Alkali extraction |
| 3.8 | pH Adjust |
| 3.9 | Drain Press |
| 3.10 | Filtration |
| 3.11 | Suspended solids 34 Kg |
| 3.12 | NaOH 0.5% 40 Kg |
| 3.13 | Drying |
| 3.14 | Solids 2 Kg |
| 3.15 | Cake 4 Kg |
| 3.16 | DIE 4 Kg |
| 3.17 | T = 10° C. t = 1 h pH = 9.0 |
| 3.18 | 26 L Liquid |
| 3.19 | 30 L Liquid |
| 3.20 | Nitric acid 1% 40 Kg |
| 3.21 | DIE 4 Kg |
| 3.22 | Filtration |
| 3.23 | Suspended solids 20 Kg |
| 3.24 | 14 L |
| 3.25 | Homogenization pH adjust |
| 3.26 | Alcohol precipitation |
| 3.27 | ETOH96% 31.2 Kg |
| 3.28 | Filtration |
| 3.29 | EOH 70% + Sol. 65.2 Kg |
| 3.30 | 6 Kg |
| 3.31 | Homogenization |
| 3.32 | Amonium Buffer pH 6.0 |
| 3.33 | Enzymatic reaction |
| 3.34 | T = 20° C. t = 12 h pH = 6.0 |
| 3.35 | Laccase 18 mg/ml 1 ml |
| 3.36 | Alcohol precipitation |
| 3.37 | ETOH 96% 3.9 Kg |
| 3.38 | Filtration |
| 3.39 | ETOH 70% + Solubles 9.9 Kg |
| 3.40 | Solids 5 Kg |
| 3.41 | Drying |
| 3.42 | Modified Pectin 170 g |

With the information in the mass balance, we calculated the yield of extraction from wet preserved pulp, taking into account that the wet pulp is 75% moisture, the total solid content is just 2.5 Kg. After drying the final gel, the pectin in mass was just 170 g. This give us only a 6.8% of yield. By revising the process, the most clear losses of polysaccharides could be in the filtration steps. The suspended solids have a high content of protein and carbohydrates as mentioned before. However, these particulates do not solubilise at pH between 3.5 and 7.0 which is the pH range for pectin stabilization. Other factor that lowers the yield is the extraction of the soluble solids. In the laboratory we measure the content of water soluble but alcohol insoluble solids (Soluble fibretable 7), this analytical method makes correction for protein content (AOAC 985.29 18th edition) and its value is a good approximation of the content of pectic material. The 170 g of pectin yield from the 10 Kg of wet pulp (6.8% in dry basis) is less than half of soluble dietary fibre (12%) in the coffee pulp. Also is important to mention that the colour of the pectin extracted is very dark, which could indicate the presence of flavonols which reduce the content of sugars in the total mass. Much work is still to be done in the extraction and purification of pectin from coffee pulp.

The reproducibility of the laboratory method for extracting coffee pulp pectin was tested and the results agrees with the previous extractions. Though the method is reproducible, there still much to improve in the extraction parameters and filtration techniques to increase yields, new methods for pectin extraction use in other plant materials like steam explosion, microwave or high pressure extractions could improve the yields of pectin. Other aspect to research further is the purification of the pectin. Since coffee pulp have high quantity of polyphenols, is necessary to find a way to remove them so the pectin can be used in food applications without given colour shifts.

To avoid the rapid oxidation of coffee pulp, we can use sodium sulphite solution to collect and store the biomass. The sulphite solution shows an anti-oxidative effect when applied to the coffee pulp. This method can be scaled-up quickly and seems to be cost effective for larger quantities of biomass. We also blanched and dried the biomass to avoid fermentation. After drying, the pulp is stable and could be shipped everywhere where the extraction process is implemented. The quality and applicability of the coffee pectin extracted from preserved and dried pulp should be tested in the future to confirm the usefulness of this method.

In the scaling up of the process we encounter several hurdles that need attention in future optimizations. One of the main issues is the low yields of pectin that we are obtaining from the fresh (preserved) coffee pulp. Also there is many technical problems in the filtration methods where losses are important. Finally, more attention has to be put in purification of the extracted pectin. The main focus right now should be to find optimal processes for extraction and purification avoiding the use of solvents.

The gelling properties of the coffee pectin obtained with the present invention are surprisingly good and were compared with other gellants. The gelling properties seem to be even better than arabic gum, when compared at the same concentration. Likewise, also, the gelling properties of the coffee pectin as described herein, are substantially better of sugar beet pectin (at the same concentration). It further appears that without the enzymatic treatment of the present invention, a further enzymatic modification of the coffee pectin is very difficult or even impossible. Hence, surprisingly an enzymatic modification of coffee pectin per se is very difficult or even impossible, whereas for other pectins this is no problem. Only after application of the process of the invention, including acid extraction and enzymatic modification, further enzymatic modification with other enzymes is possible.

Different sources of pectins have different molecular characteristics and different degree of methylation, or acetylation. As far as the prior art is concerned, only pectins extracted from sugar beet may show feruloyl esters attached to the pectin structure. However, in the present invention it was surprisingly found that pectin extracted with the herein described procedure from coffee pulp shows presence of phenolic compounds (ferulic acid is phenolic compound also known as cinnamic acids). Moreover, the phenolic compounds are bound to the higher molecular weight fractions of the acid soluble, alcohol insoluble cell wall material of coffee pulp. Only pectins with feruloyl groups can be cross-linked by enzymatic means using enzymes such as laccase according to the present process. Citrus pectin or apple pectin do not show feruloyl groups attached to the neutral branches of the molecule. A pectin molecule can be seen as a backbone of galacturonic acid (smooth region or HG) attached to ramified structure comprising rhamnose, arabinose and galactose unit is (hairy region or RG). Methyl groups and acetyl groups are attached to the galacturonic acid fractions, while feruloyl groups are found only in the neutral side chains. At higher pH, the methyl groups may be hydrolysed from the pectin backbone. The acetyl groups need harsh conditions to be hydrolysed (e.g. higher pH and higher temperature). At high pH, pectin structure is broken down through β-elimination mechanism, which only affects the galacturonic fractions that do not have other side groups. In summary at high pH, methyl groups are hydrolysed and the smooth region is broken in the sites where there are no other side groups. When the enzymatic modification occurs, it may especially happen through the neutral side chains in the RG region. That gives a new molecule with lower DM and higher DA. Enzymatic cross-linking of pectins can only occur where feruloyl groups are present in the molecule. From literature we know that only sugar beet pectin and now coffee pectin present this type of groups in their pectin structure. The cross linking reaction is catalysed specifically by for instance PPO (polyphenyl peroxidase) which horse radish peroxidase and laccase are part of. Therefore the technology is based in both the type of enzyme used and the source of the pectin. Sugar beet pectin structure shows an RGI type configuration in which RG represents in between 49 to 59 mg/g of dry material and a maximum of 656 mg/g of dry material of galacturonic acid when de-esterified using plant PME, while in comparison with coffee pectin RG represents only 10 mg/g dry matter and galacturonic acid represents 281 mg/g of dry matter. Hence, coffee pectin is substantially not similar to sugar beet pectin in structure. Further, coffee pectin has a higher degree of acetylation in comparison to red beet pectin. In the process to obtain coffee pectin concentration of polyphenols in both extracts are very high, it has been proven at laboratory scale that without any treatment for the reduction of active polyphenols in the pectin extract, substantially no enzymatic reaction will take place. The only reaction that is carried without any restriction is the oxidative cross linking of the pectin. So to be able to modify enzymatically pectin in a coffee matrix (pectin from coffee) is to remove amongst other the tannins or make them react as described herein. Without laccase and/or other oxidoreductase it may not be possible to do other enzymatic reactions on coffee pectin.

As experimental conclusion coffee pectin can be extracted from coffee pulp with good yields. Moreover, coffee pectin can be chemically or enzymatically modified to produce pectins with acceptable gelling properties. The polyphenols in the extracted pectin show an (optical) absorbance wavelength shift with increasing pH, and this strongly indicates the presence of polyphenols in complex networks like flavonoids. Therefore possible feruloy esterified neutral side chains are plausible in the structure.

Commercially available pectins are characterized by a high content of polygalacturonic acid, the legal definition for pectin used as a food additives or for pharmaceutical purposes requires that at least 65% of the ash and moisture free content be galacturonic acid. This requirements limits the potential sources of food and pharmaceutical pectins. The difference in galacturonic acid between pectin sources is linked mostly to the difference in concentration of the neutral sugars that are part of the molecule, largely arabinanas and galactan moieties.

The best know property of pectin is that it forms gels with sugar and acid. This can be seen as a partial dehydration of the pectin molecule to a degree where it is intermediate between solution and precipitation. The particular structure of pectin imposes some specific constrains. High methoxyl pectin, unlike alginate, does not contain sufficient acid groups to gel or precipitate with calcium ions. At a pH well above the pK value for the acid groups, the molecule possesses sufficient negative charge to prevent gelation under practical conditions in sugar water systems. As the pH is gradually reduced, the pectin is capable of forming a gel at first at high sugar contents (around 80% in brix scale) and at gradually lower sugar contents as the pH is reduced.

One of the commercial variables of pectin structure is the acetylation and methylation pattern due to the relation of this value with the gelation behaviour. Galacturonic acid in the polymerized form, has the possibility to show methyl groups attached to the carboxylic groups. The methylation percentage is taken as the ratio of methyl groups per mole of galacturonic acid present in the pectin. Indeed one of the commercial characteristics of pectin is its degree of methylation DM. The degree of methylation separates between rapid set pectin and slow set pectin. At pH values well below 3.0 a very rapid setting pectin with degree of esterification of above 72% will form a gel with 55% or somewhat less of sugar. Slow set pectins are produce by mild hydrolysis of the ester groups to a degree between 58%-65% DM, and hence bear more charge at a given pH. In consequence the gel strength and setting temperature curves are displaced to lower pH. These pectins are used where a lower setting temperature is required, or where the rate of set would otherwise be too high because of the increased sugar solids of the product. Low methoxyl pectins are produced by de-esterification to a point where less than 50% of the total carboxyl groups are esterified. If this process is carried out using acid or alkali, the balance exists as free acid groups; these pectins are termed conventional or non amidated low methoxyl pectins. Alternatively, pectin may be reacted with ammonia, usually by a heterogeneous reaction in an alcohol suspension. This reaction produces amidated pectin containing acid amide groups in addition to acid ester groups. Both types of low methoxyl pectins are believed to gel in an egg-box mechanism with calcium ions.

In conclusion, pectins that can be modified by enzymes to meet specific degrees of methylation and acetylation like the coffee pectin described here, allow to meet different types of setting properties as well as different behaviours when gelling, therefore the pectin obtained with this process can be tailored for different applications.

Hence, the invention also provides a process for producing a pectin based product comprising using the (polyphenol functionalized) coffee pectin extract obtainable by the process as defined herein (and/)or the (polyphenol functionalized) coffee pectin extract as defined herein and processing the (polyphenol functionalized) coffee pectin extract together with one or more other components into the pectin based product. For instance, the pectin based product may comprise a food product. In another embodiment, the pectin based product comprises a pharmaceutical product. In yet another embodiment, the pectin based product comprises a neutraceutical product. The term "pectin based product" may relate to any product comprising the (polyphenol functionalized) coffee pectin extract, even when the amount is low. The one or more other components may be any other component necessary to make such food product, pharmaceutical product or neutraceutical product, respectively.

Figure 6A:
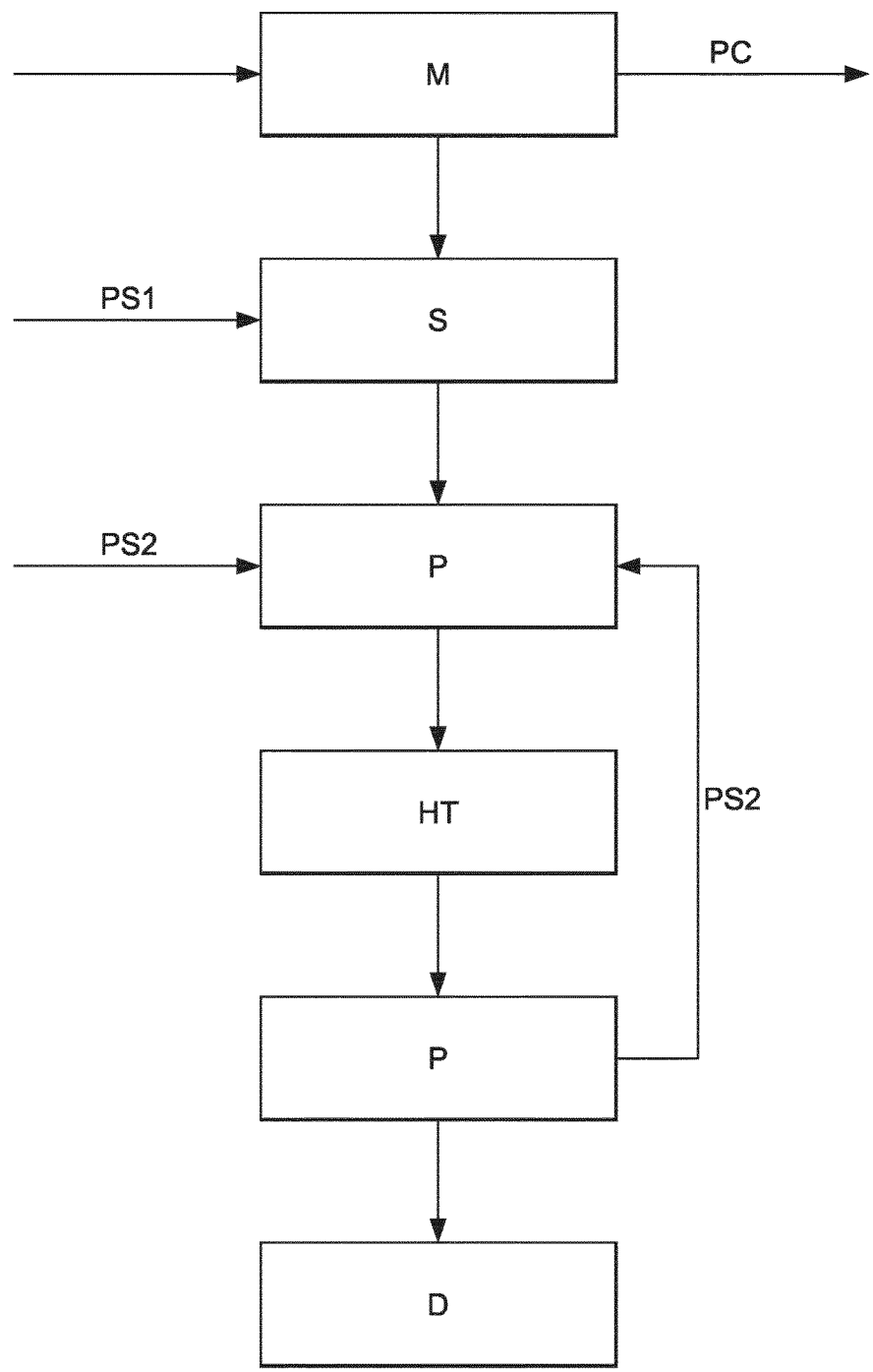
FIGS. 6a-6b and 7 show some further aspect (see also below). The schematic drawings herein are not necessarily on scale.

Here below, further preservation of coffee pulp/husk to inhibit fungal growth and oxidation of phenolic compounds is described. FIG. 6a schematically depicts a process to preserve coffee pulp collected from wet mills or husk of coffee pulp obtained by the coffee dry method of production. Coffee cherries are used as input, which may be milled, indicated with reference M, especially pulping wet milling; the product thereof is amongst other parchment coffee (PC), that is removed from the process, and coffee pulp (CP), that is further processed. After stabilization, indicated with reference S, preservation P may take place. References PS1 and PS2 refer to the above described first and second preservation liquid. Subsequently, a heat treatment HT mak take places, and then a pressure stage P may be included. Thereafter, the preprocessed coffee pulp is dried in a drying stage (D), whereby the preserved coffee pulp is obtained. This process is further describes with reference to a specific example:

Processing Example

Fresh coffee pulp/husk from the wet mill of coffee cherries, is processed by collecting the material and adding enough preservation solution 1 (PS1) (1:3 volumes solution to pulp ratio) to cover all the pulp/husk. The material is left there for a period of 3 hours to 72 hour (optimum is 12 hours).

After the resting period of the pulp/husk, the solution is then adjusted to pH 2 using preservation solution 2 (PS2) (1 par of PS2 per 4 parts of total volume), the pulp/husk in PS2 is left to rest for 0.5 to 3 hours (optimum is 30 minutes) after the resting period the pulp/husk is heated to a temperature between 70° C. and 90° C. degrees (80° C. is the optimum) and kept at this temperature for between 10 to 30 minutes (15 minutes is the optimal). After the heating step the pulp/husk is subjected to a physical stress between 5-20 bar (optimum 10 bar) in which the liquid is drained from the biomass. The biomass is then dried, e.g. by sun drying or by mechanical drying. The drained liquid can be optionally recirculated.

An alternative to the physical stress and drying is the use of a pelletizer for the biomass at high temperatures. In this case the pulp/husk is drained from excess of water leaving the material with a water content between 5-50% of water in dry basis (optimum 15% water content). The drained coffee pulp/husk is then added to the pelletizer machine working at a temperature of between 7090° C. (optimum is 80° C.) which transforms the biomass in pellets of 5 mm diameter. An alternative to the heating and physical stress is the extrusion of the coffee pulp. The extrusion process consist of the use of commercial biomass briquette machines working at lower temperatures than the normal (between 120-180° C.) and pressures ranging between 10-150 bar (optimum 50 bar).

An alternative to heating and physical stress is the use of a briquetting machine for the coffee pulp/husk. After immersion of the pulp/husk in PS1 and adjusting the pH with PS2 the pulp/husk is drained to have a material with a water content between 5 and 20 percentage in dry basis (optimum is 12%).

TABLE 16

Preservation solution 1 (PS1) in water

| Salt compound | Minimum concentration % | Maximum concentration % | Optimum % |
| --- | --- | --- | --- |
| Sodium bisulfite | 0.01 | 5 | 1 |
| Calcium chloride | 0.1 | 10 | 1 |
| Sodium ascorbate | 0.01 | 1 | 0.5 |

TABLE 17

Preservation solution 2 (PS2)

| Acid compound | Minimum concentration % | Maximum concentration % | Optimum % |
| --- | --- | --- | --- |
| Nitric acid | 5 | 50 | 20 |
| EDTA | 0.1 | 50 | 10 |

Especially, the pulp/husk has to be submerged in PS1 solution, experimentation showed that if the pulp is not covered completely by the solution, fungi grows in the pulp not covered by the solution. When only preservation solution step one (PS1) is used the polyphenols of the coffee pulp reacts with the sulfites changing the color of the pulp to a yellow brown hue. Moreover when pressed and left to dry, fungal growth occurs. Fungal growth is not desired since it could lead to the development of mycotoxins such as ochratoxins, aflatoxins and so on. Moreover since coffee is a seasonal crop, it has peaks in production and huge quantities are produced making necessary a process to stabilize the product in situ. Therefore PS1 is not efficient if transformation of industrial quantities of coffee pulp/husks needs to be processed.

The function of PS1 treatment is to react with the already formed o-quinones and inhibit the formation of new quinones by reduction of enzymatic activity. At the same time soluble divalent cations such as calcium chloride will reduce the amount of pectins lost in the solution. The final ingredient in the compound is sodium ascorbate to minimize oxidation.

The second step is to drain the PS1 and replace it with water or optionally use the same solution as starting point, the pH of the solution is set to 2, for such effect we use PS2 which is composed by an acid such as one or more of citric acid, lactic acid, nitric acid, sulfuric acid, phosphoric acid, hydrogen chloride, among others. Further, optionally EDTA may be added as preserving agent. The best results has been with organic acids such as citric acid and lactic acid. The pH of the solution is changed using a concentrated solution of any of this acids and EDTA in a concentration of 5% EDTA and 20% acid (called PS2). The final acid concentration of the solution in which the pulp is submerged is between 1% and 10% of acid. The material is then left to rest for couple of hours (1-2 hours). During this time the sulfite gets unstable and is transformed into $SO_2$, while the polyphenols are activated again. Since coffee PPO has an optimum pH of 7, the low pH of the solution inhibit the oxidation of the polyphenols. At the same time the EDTA reduces other forms of oxidation. This step can be performed as only measure for preserving the pulp, however better results are achieved when used in combination with PS1.

After both steps undesired compounds of coffee, such as o-quinnones, do not form. We have discovered and tested that coffee pulp can stay in the preservation step for over 72 hours without any fermentation or fungal growth (under not yet optimized conditions). Moreover, the polyphenols that in normal conditions are oxidized regain the bright red color, while with the use of sulfite compounds alone this does not occur.

After both steps, the pulp needs to be heated to at least 70° C., preferable 80° C. and not exceeding about 90° C. at atmospheric pressure. This heating may inactivate substantially all endogenous enzymes of coffee pulp/husk, at the same time polyphenols are activated by the low pH, they will inhibit thermal oxidation of the material. After the heat treatment coffee pulp/husk is stable to be dried or be processed further.

Especially good results include the combinational use of a sulfite solution and an acid solution followed by a heat and stress treatment in the order and proportions described to stabilize the pulp and inhibit any type of oxidation or degradation by the endogenous enzymes present in coffee pulp/husk. The final product is a stable coffee pulp pretreated to optimize extraction yields on further processing.

We have tested both methods of preservation of coffee pulp, one using only sodium bisulfite at 1% concentration and dipping the pulp in the solution for 3 h. After pressing the pulp to remove as much water as possible and ultimately spreading the pulp on sun drying patios. We also used our formulation, dipping the pulp in PS1 for 3 h, changing the solution for water and adding drop wise PS2 until pH is 2.5. Heating the solution to 70 C for 25 min then pressed and draining all the water from the pulp, finally spreading it on sun drying patios.

First difference is the growth of fungi in the pulp that was treated only with a sodium sulfite solution. While the pulp that was treated with PS1 and PS2 showed no fungi growth. The second main difference was the drying time of the pulp. For the sulfite treated pulp the time to reach a water activity of 0.80 aw was 4 days, while the time needed for the pulp to reach the same water activity with the treated solution PS1 and PS2 was less than 24 hours (16 hours) this is due to the change in pH of the cell wall matrix which at lower pH has lower water binding capability. The last difference is the color of the pulp itself. The sulfite treated coffee pulp has a yellow color while the pulp treated with our process show a bright red color, this is due to the activation of the polyphenols from the acid solution and the inactivation of the enzymes by the heat treatment Preservation Tests To understand the oxidation development of phenolic compounds present in coffee pulp, it was necessary to extract the enzyme(s) that catalyse the reaction while avoiding the oxidation of such compounds.

PPO enzymes from coffee showed two distinctive bands in a SDS-PAGE (sodium dodecyl sulfate polyacrylamide gel electrophoresis), these bands are in 64 and 29 kDa of size. The purified PPO showed higher affinity with chlorogenic acid ($K_m$=0.14 mM) DOPA ($K_m$=1.36 mM), catechol ($K_m$=4.75 mM) and pyrogallic acid ($K_m$=6.16 mM) respectively. Although it was expected that chlorogenic acid has more affinity to PPO, the oxidation of this compound proceeds faster than other phenols such as catechol. It was decided to use catechol to have a better control in oxidation process, also the color formation of catechol has been used by other authors due to its increase in absorbance at 420 nm when oxidized. We decided to extract all enzymes complex of the pulp and follow the oxidation of catechol as substrate using the enzyme extract. When subjected to concentration of the enzymes from the coffee pulp it is important to mention that the retentate in the Amicon membrane was a dark brown colour. In the extraction PVPP was used to bound mono and diphenols that could be in solution. After centrifugation, it was visible that many of the color compounds in the coffee pulp extract are retained, this could mean that polyphenols are bound to bigger molecules like proteins and polysaccharides. The colored compounds did not elute through the membrane which should let pass molecules smaller than 10 kDa. Because the objective was to test the inhibition of the enzyme(s) by addition of chemicals (sodium bisulfite, organic acids) or by temperature treatments in processing circumstances, we kept all possible enzyme sizes that can have an effect in the oxidation of polyphenolic compounds. The extract of the enzyme was used as it was extracted from the Amicon membrane, and suspended in 50 mM phosphate buffer at pH 6.

Inhibition In Vitro:

To calculate the oxidation inhibition, the change in absorbance after 24 h of the solution with enzyme and substrate was compared with the change of absorbance of the samples with sodium bisulfite solution, nitric acid, citric acid or when temperature was applied. For the inhibition with sodium bisulfite, there was a decrease in the absorbance of the enzyme extract solution without added catechol. There is a clear interaction of the bisulfite solution with the colored compounds in the coffee enzyme extract. This also reinforces the idea that polyphenols could be part of bigger molecules that were not eluted through the Amicon membrane. Or the polyphenols themselves are polymers bigger than 10 kDa. Interactions of proteins and polysaccharides with polyphenols such as resorcinol and catechol have been studied in the past. The interactions of bovine serum albumin (BSA) with catechol show that complexation is reversible, and is driven by nonspecific surface phenomena. This complexation occurs via both hydrogen bonding of the polyphenol to the exterior ketoimide, and polar groups on the protein and hydrophobic interactions. These mechanisms may be dependent of the protein concentration and the pH of the aqueous solution. Polyphenols concentrations in coffee pulp are higher than in other plants such as apples and pears. Protein was also analyzed in the fresh coffee pulp and it was found to be 8% (dry weight based). If proteins from the same coffee extract go into solution when blending, the polyphenols could bind to the proteins. The extraction takes place at a pH where the binding of polyphenols to proteins such as BSA have been found to be favorable, the same binding process could happen with the proteins from the coffee pulp.

TABLE 18

Light absorbance measured at 420 nm after 12 h for the oxidation of catechol (substrate) in absorbance units (AU)

| Treatment | Substrate blank (AU) | Enzyme extract blank (AU) | Oxidation reaction (AU) | Change on (AU) after treatments |
|---|---|---|---|---|
| None | 0.072 | 0.158 | 0.385 | 0.227 |
| Sodium bisulfite | 0.063 | 0.095 | 0.083 | −0.012 |
| Nitric acid | 0.135 | 0.169 | 0.200 | 0.031 |
| Temperature | 0.137 | 0.171 | 0.184 | 0.015 |
| Citric acid | 0.100 | 0.135 | 0.159 | 0.024 |
| Sodium bisulfite + citric acid | 0.145 | 0.175 | 0.198 | 0.013 |
| Citric acid + temperature | 0.129 | 0.135 | 0.137 | 0.002 |

Sulfite compounds can be used to avoid oxidation in foodstuff. The coffee enzyme extract oxidizes catechol, but in the presence of sodium bisulfite the oxidation is stopped as is showed in Table 18. The coffee extract is a mix of naturally occurring endogenous enzymes; PPO is present in this extract. The oxidation of catechol shows that the main reaction contributing to browning of the coffee pulp is the oxidation catalyzed by the PPO.

The pH of the solution is important for PPO to be active. In Table 18 it is shown that a treatment with nitric acid at concentrations up to 100 mM inhibits oxidation but do not reverse the o-quinones formed during the initial oxidation process. Moreover, other tests had shown that pH inhibition as well as sulfite inhibition is reversible.

Elevation of the temperature is another way to stop browning of fruits and vegetables. PPO may be inactivated when subjected to temperatures over 50° C. As the majority of processes for thermal inactivation are intended for fresh fruits and vegetables, it is desirable to expose the product as less as possible to higher temperatures in order to preserve appearance of the product. In the case of coffee pulp, the inhibition of the enzymatic browning is desired for preservation of the biomass so posterior processes can be applied. As appearance or texture of the product is not of importance, coffee pulp can be subjected to higher temperatures and longer times. However, the impact of such treatments on the final quality of pectin has to be assessed. It was decided to heat the coffee enzyme extract for 30 min and 90° C. so to mimic a normal blanching step for the pulp, in such way not only PPO but other enzymes as well as fungal activity will be stopped. As can be seen in table 18, temperature also inhibits enzymatic browning, however it also catalyzed oxidation therefore the change in absorbance between the substrate blank, the enzyme blank and the oxidation sample. The higher absorbance compared to the sulfite could be due to the non enzymatic oxidation of the polyphenols present in the coffee extract as well as the oxidation of catechol by the presence of oxygen. In any case, temperature could be applied in coffee pulp to stop enzymatic browning. As such or in combination with an acid (nitric or citric) to have better results as its shown in table 19.

In the post-harvest process, where coffee cherries are separated from the beans, it is generally accepted that if the coffee cherry contains enough water to support mould growth and OA formation it will occur in the initial 3-5 days of drying. The coffee pulp should spend no more than 4 days drying to a water activity (aw) below 0.80.

Sulfite treatment can stop fungal growth, if concentrations of sulfites are high enough to inhibit contamination. However, since sulfites are not stable, the inhibition of fungal contamination is also unstable with sulfites. Moreover, coffee pulp from wet mills contains high amounts of water which increases the time needed to reduce the water activity to 0.80 aw, making the pulp prone to contamination with fungi.

Mycotoxin is indicative of fungal growth. The different procedures were tested on mycotoxin, see table 19.

TABLE 19

Mycotoxin analysis of coffee pulp

| Mycotoxin | Non treated CP | Sulfite treated CP | PS1 and PS2 treated CP |
|---|---|---|---|
| Ochratoxin | 450 mg/kg | 100 mg/kg | n.d. |
| Aflatoxins | 250 mg/kg | 50 mg/kg | n.d. | n.d. non detectable, lower limit of detection 1 mg/kg

Figure 6B:
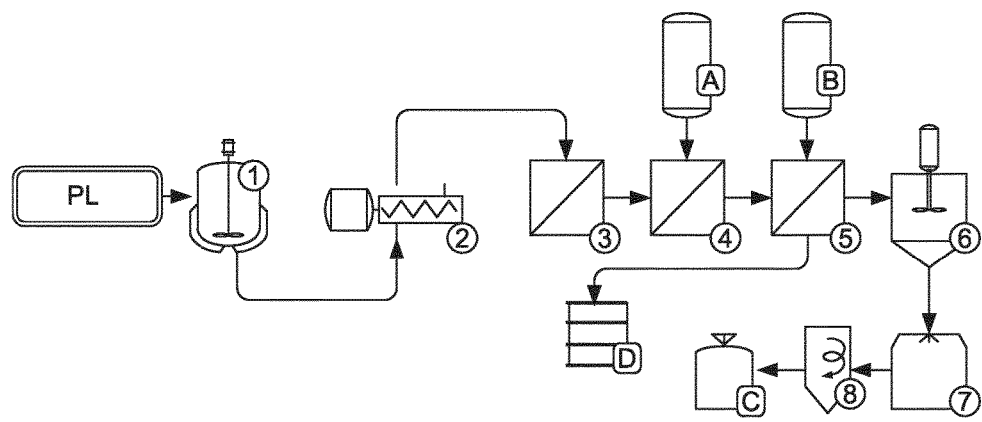

Below, and with reference to FIG. 6b, purification of coffee pectin by ultrafiltration is further elucidated. FIG. 6b is a schematic drawing of an embodiment of the purification process of coffee soluble pectic compounds after acid or acid and alkali extraction process. Reference PL indicates pectin liquor (i.e. material after acid or alkaline extraction having a Brix of 5%. In this drawing, reference 1 indicates a conditioning tank, reference 2 a screw pump, reference 3 ultrafiltration, reference 4 diafiltration with acid, reference 5 diafiltration with water, reference 6 pH adjusting the tank, reference 7 a spray drayer and reference 8 a cyclone. Further, reference A indicates a 0.1 N organic acid, reference B indicates RO (reverse osmosis) water, reference C indicates purified pectin, and reference D indicates polyphenols.

Preconditioning and Extraction

The pectin liquor is the extracted material from the acid extraction as described above. The extracted liquid is filtered to remove solid particles. The extracted liquid must be adjusted to a pH exactly of 2.4 with preferably an organic acid such as citric acid or lactic acid at 0.1N concentration, but inorganic acids such as nitric hydrochloric and phosphoric are also possible. The extracted liquid then is heated to a temperature over 50° C. but not exceeding 70° C. The liquid then is subjected to the ultrafiltration process.

Ultrafiltration

Ultrafiltration of the coffee pulp soluble extract is done with polymeric or ceramic membranes. Good results have been achieved using polymeric membranes such as modified polyethersulfone (mPES). But other membranes such as aluminum oxide, titanium dioxide, or silica are also possible. The pore size of the membrane should be in between 50.000 Da and 150.000 Da cut off, best results have been achieved with pores size of 70.000 Da cut off. The membranes can be of different geometries such as tubular, wounded spiral, and flat sheet or equivalent. As well as configurations such as cross-flow filtration, tangential flow filtration or dead end filtration. Tests have been done at pilot scale with flat sheet membranes and with tubular membranes in tangential flow arrangement and flat sheets in dead end configuration.

The coffee extract is obtained as described above, preferably at least the acid fraction must be used. The pH of the soluble coffee extract is set to 2.4 or lower with preferably an organic acid such as citric acid or lactic acid. The solution is kept in all the process over 50° C. but not exceeding 70° C. to avoid breakdown of the pectin structure this is denominated the feed of the ultrafiltration and diafiltration process. The membrane pore size must have a cut off of minimum 50.000 Da. The extracted solution is best used without any enzymatic modification for optimal process. The transmembrane pressure will be in a range between 3 Bar to 10 Bar in the whole operation. Also innovative of this process is the fact that from the membrane permeate the resulting fraction has high concentration of polyphenols more than 50 g/kg that could be recovered by later process. What has been observed in the performed tests is that although transmembrane pressure increases, fouling is not observed. This is due to the chemical characteristic of the extracted pectin as well as the conditions of extraction and purification which differs in the previous literature. During ultrafiltration is also possible to concentrate the pectin extract by recirculating the permeate fraction. The recirculation of the feed permeate, is performed at a temperature between 50 C and 70 C, and the pressure is increased to keep a stable flux. Final concentration of the feed can be between 100 g/kg to 650 g/kg of coffee pectin on the feed.

Diafiltration

After the feed has reached the desired concentration, a diafiltration step is especially performed to purify the coffee pectin. The process is performed in the same ultrafiltration system, the volume of the feed is kept constant by replacing the permeate volume with a solution of 0.1N citric or lactic acid on the feed. The final point of the diafiltration is when polyphenols concentration in the feed is between 10 g/kg and 100 g/kg and/or glucose content below 100 mg/kg. At this point the feed is dialyzed against water until pH reach 3.5. When the pH increases more there is a risk of fouling the membrane.

By performing the ultrafiltration and subsequently the diafiltration steps, most of the low molecular weight compounds such as sugar and polyphenols are removed from the feed. At the same time the feed becomes more concentrated on pectic substances during ultrafiltration, saving energy in subsequent dewatering and/or drying process.

From the above it is clear that coffee pectin as extracted is a new material and requires specific and innovative techniques for purification. The present invention provides an ultrafiltration process for coffee pectin extract concentration followed by diafiltration at low pH and a final purification with water.

Procedure Example:

Equipment used: Ultra/Hyper filtration test unit; 3 kW Pump: 2-10 l/min flow rate, max 80 bar; membrane cartridge discs (5, 10, 50, 100 kDa resp.) These membranes are mounted parallel:

There is one retenate. The filtrates were be collected separately. Procedure:
1. 145 litres of water were mixed with 16 kg dry preserved coffee pulp and heating to 90° C.
2. The pH of this mixture was adjusted below 2.5 by adding solid citric acid.
3. The suspension was mixed and recirculated for 3 h
4. The separation of the solids was done using a filter press.
5. The liquid was heated to 70° C. for 30 min.
6. The finer particles were removed by centrifugation.
7. The pH was stabilized to 2.5 using solid citric acid
8. The concentration of coffee pectin was done in the ultrafiltration unit until final pectin concentration (alcohol test) was 70 g/kg.
9. The pectin concentrate was dialyzed in the same ultrafiltration unit against citric acid solution 0.1N for 4 hours.
10. The dialysis was stop when glucose concentration was not detectable by the Phenol method.

TABLE 20

Data log of the ultrafiltration and diafiltration process:

| Time | TMP in Bar | Log |
| --- | --- | --- |
| 00:00 | 5 | Start of concentration |
| 01:00 | 7 | Back pressure build up |
| 01:10 | 4 | Backpressure valve relieved |
| 02:00 | 6 | Dialysis start |
| 06:00 | 8 | Glucose measurement |
| 06:10 | 8 | Replacement of acid for water on the feed |
| 07:10 | 10 | pH measurement (3.5) |
| 07:30 | 10 | Stop of process |

TMP = Transmembrane pressure buid up.

After the process the membranes were backwashed with 0.1% NaOH solution twice the volume and rinsed with plenty RO water. The membranes were used successfully after without signs of fouling.

Application of Coffee Pectin as Emulsifier and Stabilizer in Oil in Water Emulsions Coffee pectin as extracted with the process described above has different chemical characteristics compared to other traditional pectins. One of this characteristics is the degree of methylation of the acid extracted solution which is between 80% and 90%. Other major difference is the degree of acetylation of the resulting pectin which is around 150% and the mol percentage ratio of galacturonic acid to arabinose and galactose. Although many modification of the pectin can be performed with enzymes as well documented in literature, is also possible to use the coffee pectin no enzymatic modification. The resulting coffee pectin has interesting properties for applications in different industries.

Coffee pectin is extracted from preserved coffee pulp by an acid and alkali extraction but at least the acid extracted material is necessary. The extracted pectin solution from coffee pulp is filtrated to remove insoluble particles bigger than 1 microns and subjected to purification being the purified process an alcohol precipitation or an ultrafiltration process, ultrafiltration process is preferred due to the absence of residual alcohol in the final product. The purified pectin can be dried or spray dried to produce coffee pectin.

One of the applications for coffee pectin, is as emulsifier and stabilizer. Coffee pectin extracted as described above has been used to prepare oil in water emulsions and as viscosity modifier in model systems. Coffee pectin was compared against Sugar-beet pectin for emulsification properties such as oil droplet size and followed over time for stability of the emulsion. Also, coffee pectin solutions were compared against Sugar-beet pectin solutions at the same concentrations and pH for dynamic viscosity (viscosity against shear). The results shows clearly that coffee pectin presents a longer emulsion stability at accelerated shelf life test and higher viscosities than sugar-beet pectin. Moreover, coffee pectin shows shear thinning behavior whereas sugar-beet pectin does not. Therefore coffee pectin as extracted under the parameters described is innovative as a product and also its application as it has not been mentioned in previous literature as far as our knowledge goes.

Hence, in an embodiment coffee pectin may be used as emulsifier and/or stabilizer agent for oil in water emulsions. It appears that pectin extracted from coffee pulp following the methods as described herein has better emulsification performance than commercial available pectin from sugar-beet pulp. Hence, the thus obtained coffee pectin may be very well used for the stabilization of oil in water emulsions.

Comparison of Emulsification Properties of Coffee Pectin Compared to Sugar-beet Pectin:

An experiment was done, using the following materials.

TABLE 21

| Materials | | | |
| --- | --- | --- | --- |
| Ingredient | Source | Description | Remarks |
| Pectin 1 | Pectcof | Coffee SDF Pectin extracted form coffee pulp in solution 2%, galacturonic acid 1.2% on mass | Degree of methylation 90% Degree of esterification 150% |
| Pectin 2 | CPKelco | GENU BETA Pectin Highly esterified pectin extracted from sugar-beet pulp | Degree of acetylation 24% High degree of methylation >70% MW = 76.000 Da |
| Orange Oil | Sigma | Brazilian | |

1. Emulsions (150 g) were prepared with 10% of orange oil (15 g) and 90% of water phase (135 g) containing the pectin samples from sugar beet pulp and coffee pulp.
2. The coffee pectin was delivered in water (2%), and was diluted to get the right emulsifier concentration.
3. Sugar beet pectin was dissolved in hot water (85° C.) and thurraxed.
4. pH of the water phases was adjusted to pH 3.5

5. A pre-emulsion was made by mixing the emulsifier solution with the oil using an ultrathurrax (2 min, 10000 rpm).
6. Then the pre-emulsion was homogenized on a Panda lab homogenizer
7. Both emulsions were done in quadruple
8. One pair of each sample was analysed immediately for particle size distribution (PSD)
9. The second pair was stored at 37° C. for four (4) weeks, then gently shaken and analysed for PSD.
10. Solutions of sugar-beet pectin and coffee pectin of 0.5% concentration on mass were prepared in buffer solution pH 3.5 and kept at 20° C.
11. Viscosity against shear rate was measured using shear sweeps and a concentric geometry, temperature was kept constant at 20° C.

Results

TABLE 22

Emulsification properties:

| Sample | Concentration % on mass | Oil droplet size D[0.5] before storage | Oil droplet size D[0.5] after storage |
|---|---|---|---|
| Coffee pectin | 0.5 | 3.163 | 3.269 |
| Sugar-beet pectin | 0.5 | 1.476 | 10.759 |

Figure 7:
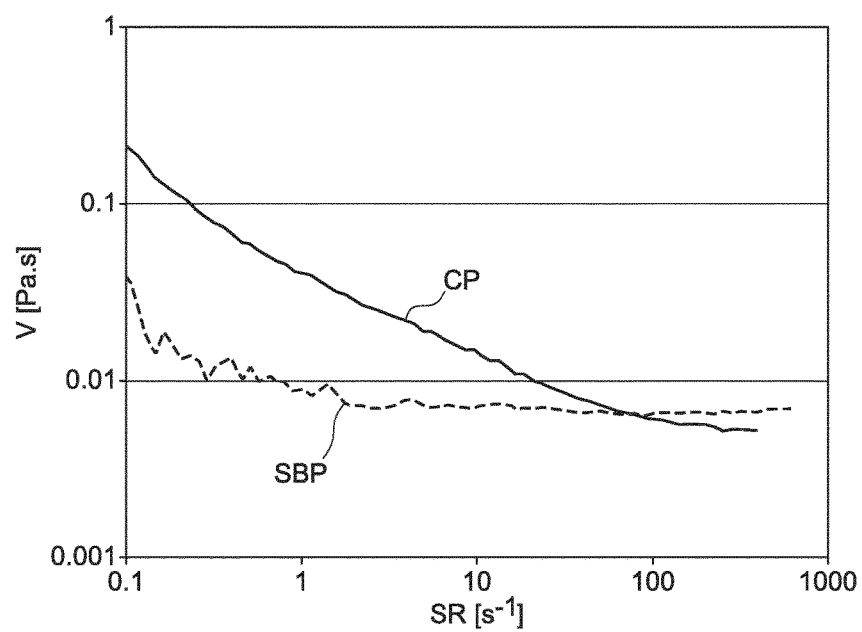

At first observation coffee pectin emulsions looked less stable and separation of two phases occurs in time when higher concentrations are tested. However a more thoughtful analysis shows that the actual cream layer is a more stable emulsion in comparison to sugar-beet pectin. When homogenized both sugar-beet pectin and coffee pectin shows a narrow distribution of the oil droplets. After the storage period coffee pectin still shows the narrow distribution of the oil droplets. In comparison, sugar beet pectin showed bimodal distribution and an increase of the droplet size of almost one order of magnitude. The stabilization properties viscosity versus shear for sugar beet pectin 0.5% (SBP) and coffee pectin 0.5% (CP) is indicated in FIG. 7, with on the x-axis the shear rate in $s^{-1}$ and on the y-axis the viscosity in Pa·s. Coffee pectin shows shear thinning behavior, while Sugar-beet pectin shows a gel type behavior. The temperature and pH of both samples where kept at the same circumstances, 20° C. and 3.5 respectively.

Further, it was found that to achieve the same emulsion droplet size d(0.5) with arabic gum one needs 15% of the emulsifier whereas with coffee pectin you need only 0.5% of the emulsifier in the same conditions. When comparing with sugar beet, the coffee pectin has longer shelf life. The droplet size is much more stable than of sugar beet pectin (see also above).

The invention claimed is:

1. A coffee pulp treatment process for preserving coffee pulp, comprising:
   a1. providing the coffee pulp, obtainable from a production process for producing green coffee beans from coffee cherries; and
   a2. subjecting the coffee pulp to a preservation process comprising:
      (i) combining the coffee pulp with a preservation liquid comprising a sulfite and a divalent cation;
      (ii) bringing the pH of the thus obtained mixture to a pH of 4 or lower; and
      (iii) removing liquid from the mixture.

2. The process according to claim 1, further comprising:
   subsequent to bringing the pH of the obtained mixture to a pH of 4 or lower, heating the mixture obtained in step (a2)(ii) to a temperature of at least 60° C., wherein removing the liquid from the mixture comprises removing the liquid from the mixture heated to at least 60° C.; and
   b. extracting from the coffee pulp a pectin comprising extract, wherein extraction is performed in a first extraction under acid conditions and in a second extraction under alkaline conditions, or in a first extraction under alkaline conditions and in a second extraction under acid conditions, to provide the pectin comprising extract.

3. The process according to claim 2, wherein after the extractions under acid conditions and alkaline conditions, the extraction process further comprises membrane ultrafiltration and diafiltration, wherein the membrane has a cut-off in the range of 50,000-150,000 Da, to provide the pectin comprising extract as permeate, wherein the pectin comprising extract after extraction under acid conditions and alkaline conditions but before membrane ultrafiltration is brought to a pH below 3.5 at a temperature in the range of 40-80° C.

4. The treatment process according to claim 1, further comprising:
   subsequent to bringing the pH of the obtained mixture to a pH of 4 or lower, heating the mixture obtained in step (a2)(ii) to a temperature of at least 60° C., wherein removing the liquid from the mixture comprises removing the liquid from the mixture heated to at least 60° C.;
   b. extracting from the coffee pulp a pectin comprising extract, wherein extraction is performed under acid conditions, to provide the pectin comprising extract;
   c. performing enzymatic treatment of the pectin comprising extract, wherein the enzymatic treatment comprises a treatment with one or more enzymes selected from the group consisting of an esterase and a reductase, to provide an enzymatically treated pectin material, wherein the enzymatic treatment further comprises a treatment with an oxidoreductase; and
   d. performing extraction of a polyphenol functionalized coffee pectin extract from the enzymatically treated pectin material.

5. The process according to claim 4, wherein the coffee pulp is subjected to a first extraction under acid conditions, leading to a first extraction product and a residual product, wherein the residual product is further subjected to a second extraction under alkaline conditions, leading to a second extraction product and a second residual product, wherein the product from this second extraction is recombined with the remaining first extraction product from the first extraction, wherein these combined pectin extraction products are then further subjected to an enzymatic treatment,
   wherein the acid conditions of the first extraction are at a pH in the range of 0.5-4,
   wherein the first extraction is performed at a temperature of at least 80° C.,
   wherein the alkaline conditions of the second extraction are at a pH in the range of 8-14, and
   wherein the enzymatic treatment comprises treatment with one or more enzymes selected from the group consisting of a laccase and a pectin-esterase.

6. The process according to claim 4, wherein the enzymatic treatment comprises a treatment with one or more enzymes in the Enzyme Class (EC) selected from the group consisting of EC 1.10 and EC 1.11.

7. The process according to claim 2, wherein the coffee pulp is subjected to a first extraction under alkaline conditions, leading to a first extraction product and a residual product, wherein the residual product is further subjected to a second extraction under acid conditions, leading to a second extraction product and a second residual product, and wherein the product obtained from this second extraction is recombined with the first extraction product from the first extraction, and wherein these combined extraction products are then further subjected to an enzymatic treatment, wherein the alkaline conditions of the first extraction are at a pH in the range of 8-14, wherein the add conditions of the second extraction are at a pH in the range of 0.5-4, wherein the second extraction is performed at a temperature of at least 80° C., and wherein the one or more enzymes are selected from the group consisting of diphenol oxidoreductase, peroxidase, laccase, pectin-esterase, methyl-esterase, poly galacturanase, endo polyglucanase, and exo polyglucanase.

8. The process according to claim 7, wherein the first extraction is performed in a first extraction liquid that comprises $H_2O_2$.

9. The process according to claim 1, wherein the preservation liquid comprises a calcium salt and sodium ascorbate, wherein the pH is brought to 3 or lower with a liquid comprising an organic acid, and wherein EDTA is added to the mixture.

10. The process according to claim 1, wherein, after the pH of the mixture is adjusted to 4 or lower, the mixture is heated to a temperature of at least 70° C. for at least 5 minutes.

11. The process according to claim 1, wherein the liquid is removed in a process comprising (i) heating the mixture of the preservation liquid and the coffee pulp, and (ii) pressing the liquid out of the mixture.

12. The process according to claim 1, wherein the pulp is submerged in the preservation liquid.

13. The process of claim 1 further comprising:
  b. extracting from the coffee pulp a pectin comprising extract, wherein extraction is performed in a first extraction under acid conditions and in a second extraction under alkaline conditions, or in a first extraction under alkaline conditions and in a second extraction under acid conditions, to provide the pectin comprising extract,
  wherein after one or more extractions under the acid conditions or alkaline conditions, the extraction process further comprises membrane ultrafiltration and diafiltration, wherein the membrane has a cut-off in the range of 50,000-150,000 Da, to provide the pectin comprising extract as permeate,
  wherein the pectin comprising extract after extraction under the acid conditions or alkaline conditions but before membrane ultrafiltration is brought to a pH below 3.5 and a temperature in the range of 40-80° C.

* * * * *